United States Patent [19]

Berliner et al.

[11] Patent Number: 5,210,076
[45] Date of Patent: May 11, 1993

[54] METHODS OF TREATING PARKINSON'S DISEASE USING MELANIN

[76] Inventors: David L. Berliner, 380 Selby La., Atherton, Calif. 94025; Robert L. Erwin, 336 Summerfield Dr.; David R. McGee, 1990 Marshall Rd., both of Vacaville, Calif. 95687

[21] Appl. No.: 609,311

[22] Filed: Nov. 5, 1990

Related U.S. Application Data

[63] Continuation-in-part of Ser. No. 331,123, Mar. 31, 1989, abandoned, which is a continuation-in-part of Ser. No. 243,736, Sep. 13, 1988, abandoned.

[51] Int. Cl.$^5$ .............................................. A61K 37/00
[52] U.S. Cl. ................................ 514/21; 424/195.1; 424/94.4; 514/567
[58] Field of Search .................... 514/567, 21; 424/95, 424/195.1

[56] References Cited

PUBLICATIONS

Cotzias et al–New Eng. J. of Medicine, vol. 276, No. 7, pp. 374–379 (1967).
Mann et al–Mechanisms of Ageing & Develop, vol. 21, 193–203 (1983).
Atscholte et al–Clinical Pharm. & Therapeutics vol. 19, No. 2, 124–34 (1976).

*Primary Examiner*—Leonard Schenkman
*Attorney, Agent, or Firm*—Limbach & Limbach

[57] ABSTRACT

The invention is directed to the treatment of degenerative diseases of tissues which have lost melanin and which share a common embryological basis as tissues of the nervous system by the administration of an active substance which causes an increased concentration of melanin in the tissue. Such active substances include melanin, melanin variants, melanin analogs, melanin derivatives, tyrosinase, tyrosinase gene, melanin-concentrating hormone and combinations thereof. Examples of such diseases include Parkinson's disease, Alzheimer's disease, retinitis pigmentosa, schizophrenia and dementia. The invention is also useful in assisting in the repair of neurons in a mammal having neuron damage by administering an effective amount of an active substance which causes an increased concentration of melanin in the neuron to aid in nerve repair. The invention is further useful in protecting a mammal from a toxin-induced disease or from the adverse effects of a toxin by administering an effective amount of the active substance described above.

5 Claims, No Drawings

METHODS OF TREATING PARKINSON'S DISEASE USING MELANIN

RELATED APPLICATIONS

This is a continuation-in-part of U.S. patent application Ser. No. 331,123, filed Mar. 31, 1989, and which is a continuation-in-part of U.S. patent application Ser. No. 243,736, filed Sep. 13, 1988, both now abandoned.

BACKGROUND OF THE INVENTION

The present invention relates to the prophylaxis and treatment of degenerative diseases of the nervous system by the administration of an active substance which causes an increased concentration of melanin, melanin precursors, melanin derivatives, melanin variants and melanin analogs in the effected nervous system tissue. Such active substances include melanin, melanin precursors, melanin derivatives, melanin analogs, melanin variants, the enzyme tyrosinase, which catalyzes the reaction wherein naturally occurring melanin precursors are converted to melanin, tyrosinase gene, melanin-concentrating hormone and combinations thereof. Examples of such diseases include Parkinson's disease, Alzheimer's disease, retinitis pigmentosa and dementia. The present invention also relates to the treatment by the administration of melanin, melanin precursors or a melanin derivative of diseases of tissues which share a common embryological basis as tissues of the nervous system. The invention further relates to a method of preventing toxin-induced neurodegenerative diseases, toxin-induced diseases, or the adverse effects of toxins, and to a method for aiding the recovery of injured neurons, by the administration of the active substance which causes an increased concentration of melanin in the effected tissue.

A. Nervous System and Epidermis

The nervous system and epidermis have a common embryological basis and several common features.

1. Embryological Basis

During gastrulation the single layer of cells comprising the blastoderm migrate and fold to form the three germinal layers—ectoderm, endoderm and mesoderm. The germinal layers are the rudiments from which organs of the plant or animal develop. The ectoderm, for example, gives rise to the epidermis, central nervous system, i.e., the brain, spinal cord, spinal ganglia and nerves, various sensory organs and neural crest cell derivatives that includes cerebro-spinal ganglia and melanocytes.

Although by definition the ectoderm is the outermost of the germinal layers, it is not long during gastrulation that by migration and invagination cells once on the surface are displaced into the interior of the developing embryo. Because nervous tissue and epidermis have a shared origin, it is not uncommon for embryologic diseases to affect seemingly unrelated organs such as brain and skin.

Another example of cell migration and invagination during development is the adrenal gland. The medulla of the gland is a highly specialized adjunct to the sympathetic nervous system and derived from the ectoderm. The cortex, on the other hand, is derived from endoderm and mesoderm. The adrenal medulla secretes the catecholamines adrenaline (epinephrine) and noradrenaline (norepinephrine).

2. Cell Structure and Coloration

Early in development, the neural crest cells lie dorsal to the neural tube. Soon they migrate laterally and ventrally, basically associating with ectodermally-derived structures as in the areas of the epidermis-dermis junction.

Melanocytes are the cells found in the skin and are epidermal derivatives that are responsible for coloration. Those cells have polygonal cell bodies and long dendritic processes that ramify between epithelial cells throughout the lower strata of the epidermis. Pigmented cells are not restricted to cutaneous structures but can be found associated with various internal structures of ectodermal origin, as in the brain, spinal cord or adrenal medulla.

3. Nervous System

Neurons have a polygonal cell body and two types of arborizing processes, the axon and one or more dendrites. One region of the brain is called the substantia nigra (for black substance) because of its highly pigmented character. Many of the neurons of the substantia nigra contain significant quantities of melanin, and it is the melanin that confers on those cells the dark coloration. It has been seen that cell death in the normal substantia nigra appears to be related to the content of neuromelanin per cell. Mann, D.M. et al., *Brain* 97, 489 (1974).

The substantia nigra is one region of the brain that is involved in the coordination (planning and programming) of neural signals for gross and slow, steady movements (ramp movements) and posture. The substantia nigra is part of that portion of the brain known as the basal ganglia which is itself part of the midbrain.

Two other highly pigmented areas of the brain are the locus ceruleus and the pituitary gland. The locus ceruleus is an eminence in the superior angle of the floor of the fourth ventricle. The hypophysis (pituitary gland), like the adrenal gland, arises from two embryological sources. The anterior pituitary arises as an epithelial outgrowth from the roof of the mouth. One of the hormones that it secretes is melanocyte stimulating hormone. The posterior pituitary is derived from a downgrowth of hypothalamic nerve tracts.

B. Degenerative Diseases of the Nervous System

The term "degenerative" as applied to diseases of the nervous system is used to designate a group of disorders in which there is gradual, generally symmetric, relentlessly progressive wasting away of neurons, for reasons still unknown. Many of the conditions so designated depend on genetic factors and thus appear in more than one member of the same family. This general group of diseases is therefore frequently referred to as heredodegenerative. A number of other conditions, not apparently differing in any fundamental way from the hereditary disorders, occur only sporadically, i.e., as isolated instances in a given family. For all diseases of this class William Gowers in 1902 suggested the now-familiar term "abiotrophy," by which he meant "defective vital endurance" of the structures affected, leading to their premature death. This term, of course, tells nothing of the true nature of the defects. It is to be assumed that their basis must be some disorder of the metabolism of the parts involved.

Within relatively recent times there has been some elucidation of the nature of a number of metabolic nervous disorders which, in their symmetric distribution and gradually progressive course, resemble the degenerative diseases under discussion. It is to be expected that with advances in knowledge others of the latter group will eventually find their place in the metabolic category. The degenerative diseases of the nervous system manifest themselves by a number of common syndromes easily distinguished by their clinical attributes, the recognition of which can assist the clinician in arriving at the diagnosis of a disorder of this class.

1. General Considerations

It is a characteristic of the degenerative diseases that they begin insidiously and run a gradually progressive course which may extend over many years. The earliest changes may be so slight that it is frequently impossible to assign any precise time of onset. However, as with other gradually developing conditions, the patient or his family may give a history implying an abrupt appearance of disability. This is particularly likely to occur if there has been an injury, or if some other dramatic event has taken place in the patient's life, to which illness might conceivably be related. In such a case, skillful taking of the history may bring out that the patient or family has suddenly become aware of a condition which had, in fact, already been present for some time but had passed unnoticed. Whether trauma or other stress may bring on or aggravate one of the degenerative diseases is still a question that cannot be answered with certainty. From all that is known it would seem highly improbable that this could happen. In any event, it must be kept in mind that the disease processes under discussion by their very nature develop spontaneously without relation to external factors.

Family history of degenerative nervous diseases is a significant feature of this class of diseases. Another significant feature is that in general their ceaselessly progressive course is uninfluenced by all medical or surgical measures. Dealing with a patient with this type of illness is often, therefore, an anguishing experience for all concerned. Yet symptoms can often be alleviated by wise and skillful management, and the physician's kindly interest may be of great help even when curative measures cannot be offered.

The bilaterally symmetric distribution of the changes brought about by these diseases has already been mentioned. This feature alone may serve to distinguish conditions in this group from many other diseases of the nervous system. At the same time, it should be pointed out that, in the earliest stages, greater involvement on one side or in one limb is not uncommon. Sooner or later, however, despite the asymmetric beginning, the inherently generalized nature of the process asserts itself.

A striking feature of a number of disorders of this class is the almost selective involvement of anatomically or physiologically related systems of neurons. This is clearly exemplified in amyotrophic lateral sclerosis, in which the process is almost entirely limited to cortical and spinal motor neurons, and in certain types of progressive ataxia, in which the Purkinje cells of the cerebellum are alone affected. Many other examples could be cited (e.g., Friedreich's ataxia) in which certain neuronal systems disintegrate, leaving others perfectly intact. An important group of the degenerative diseases has therefore been called "system diseases" ("progressive cerebrospinal system atrophies"), and many of these are strongly hereditary. It must be realized, however, that selective involvement of neuronal systems is not exclusively a property of the degenerative group, since several disease processes of known cause have similarly circumscribed effects on the nervous system. Diphtheria toxin, for instance, selectively attacks the myelin of the peripheral nerves, and triorthocresyl phosphate affects particularly the corticospinal tracts in the spinal cord as well as the peripheral nerves. Another example is the special vulnerability of the Purkinje cells of the cerebellum to hyperthermia. On the other hand, several of the conditions included amonq the degenerative diseases are characterized by pathologic changes that are diffuse and unselective. These exceptions nevertheless do not detract from the importance of affection of particular neuronal systems as a distinguishing feature of many of the diseases under discussion.

Since etiologic classification is impossible, subdivision of the degenerative diseases into individual syndromes rests on descriptive criteria, based largely on pathologic anatomy but to some extent on clinical aspects as well. In the terms used to designate many of these syndromes, the names of a number of distinguished neurologists and neuropathologists are commemorated. A useful way of keeping in mind the various disease states is to group them according to the outstanding clinical features that may be found in an actual case. The classification outlined in Table 1 is based on such a plan.

TABLE 1

Clinical Classification of the Degenerative Diseases of the Nervous System

I. Syndrome in which progressive dementia is an outstanding feature in the absence of other prominent neurologic signs
   A. Diffuse cerebral atrophy
      1. Senile dementia
      2. Alzheimer's disease
   B. Circumscribed cerebral atrophy (Pick's disease)
II. Syndrome in which progressive dementia is combined with other neurologic signs
   A. Principally in adults
      1. Huntington's chorea
      2. Cerebrocerebellar degeneration
   B. In children and adults
      1. Amaurotic family idiocy (neuronal lipidoses)
      2. Leukodystrophy
      3. Familial myoclonus epilepsy
      4. Hallervorden-Spatz disease
      5. Wilson's disease (hepatolenticular degeneration, Westphal-Strumpell pseudosclerosis)
III. Syndrome chiefly manifested by gradual development of abnormalities of posture or involuntary movements
   A. Paralysis agitans (Parkinson's disease)
   B. Dystonia musculorum deformans (torsion dystonia)
   C. Hallervorden-Spatz disease and other restricted dyskinesias
   D. Familial tremor
   E. Spasmodic torticollis
IV. Syndrome chiefly manifested by slowly developing ataxia
   A. Cerebellar degenerations
   B. Spinocerebellar degenerations (Friedrich's ataxia, Marie's hereditary ataxia)
V. Syndrome with slowly developing muscular weakness and wasting
   A. Without sensory changes; motor system disease
      1. In adults TABLE 1-continued Clinical Classification of the Degenerative
Diseases of the Nervous System a. Amyotrophic lateral sclerosis
      b. Progressive muscular atrophy
      c. Progressive bulbar palsy
      d. Primary lateral sclerosis
   2. In children or young adults
      a. Infantile muscular atrophy (Werdnig-Hoffmann disease)
      b. Other forms of familial progressive muscular atrophy (including Wohlfart-Kugelberg-Welander syndrome)
      c. Hereditary spastic paraplegia
 B. With sensory changes
   1. Progressive neural muscular atrophy
      a. Peroneal muscular atrophy (Charcot-Marie-Tooth)
      b. Hypertrophic interstitial neuropathy (Dejerine-Sottas)
   2. Miscellaneous forms of chronic progressive neuropathy
VI. Syndrome chiefly manifested by progressive visual loss
 A. Hereditary optic atrophy (Leber's disease)
 B. Pigmentary degeneration of the retina (retinitis pigmentosa)

2. Parkinson's Disease

Perhaps the disorder the general public is most familiar with is Parkinson,s disease, or paralysis agitans. In early stages of the disease, there may be slight disturbances of posture, locomotion, facial expression or speech. The manifestations may be asymmetric, e.g, a slight tremor of the fingers on one hand at rest. The symptoms then become bilateral and the patient tends to assume a stooped posture. Gait disturbances increase and there is a moderate generalized disability. After a number of years the disability, bradykinesia, weakness and rigidity progress to the point of complete invalidism.

Because of the prevalence of Parkinson's disease, it has been the focus of much neurological research. As early as 1953 it was recognized that it was common for there to be a depletion of dopaminergic transmission and a loss of the melanin-containing cells of the substantia nigra. It is not fully clear whether the changes are the result of "demelanination" by cells or actual cell death.

Current therapy for Parkinsonism is the oral administration of levodopa (L-dopa), which is 3-(3,4-dihydroxyphenyl)-L-alanine. Because L-dopa is a precursor of epinephrine and melanin there are certain contraindications. Apparently levodopa can exacerbate malignant melanomas or other skin lesions and can have untoward effects in patients with cardiovascular or pulmonary disease, asthma, or renal, hepatic or endocrine disease.

The deficiency of dopamine synthesis that characterizes Parkinsonism prompted the notion of transplanting dopamine neurons, particularly those of the adrenal medulla, into the brain as replacement therapy. Following successful transplants and alleviation of symptoms in the rotational rat model and in primates with induced lesions, the first transplants of fetal adrenal medulla were made to the striatum in two patients with severe Parkinsonism. Some rewarding effects were registered. Additional successful cases have been reported in the literature. Nevertheless, it is a complicated procedure which requires fetal donor tissue, and there have been a few unexplained deaths in those same studies.

3. Alzheimer's Disease

Alzheimer's Disease (AD) generally presents a clinical picture of gradual loss of intellectual capabilities. The incidence of AD in a number of surveys averages between four and five percent of the U.S. population. This translates to approximately 1.3 million cases of severe AD and an additional 2.8 million patients with mild to moderate impairment. The diagnosis of AD is complicated by the lack of a specific clinical marker. Currently a physician must depend on longitudinal observation for the gradual manifestation of the typical neuropathological features, and the support of a diffusely slow electroencephalogram, reduced cerebral blood flow and particular patterns on positron emission tomographic scanning.

Post-mortem examination of the brain shows a generalized atrophy. There are extensive histologic changes in AD dominated by the presence of intracellular amyloid plaques and neurofibrillary tangles. Plaques and tangles are rare, however, in the basal ganglia and substantia nigra. Many specimens from AD patients demonstrate a loss of pigmentation in the area of the locus ceruleus, which is a major source of noradrenergic synthesis in the brain.

Proposed treatments for Alzheimer's disease include the administration of memory-enhancing compounds such as those described in U.S. Pat. No. 4,752,610, as well as the administration of substances such as gangliosides and peptide growth factors which aid the regeneration of injured nerve cells (Terry, R.D. et al., Ann. .Neurol. 14, 497 (1983)).

4. Schizophrenia and Other Diseases

Dopaminogenic neuronal activity may be abnormal in cases of schizophrenia. There is a reduction in fresh volume of substantia nigra in brains of schizophrenics with the majority of that due to a reduction of cell body volume in the medial portions of that region. Nevertheless, the reduction by cells is not as contributory to the fresh volume loss as is reduction of the neuropil. It is unknown whether those observations have a bearing on the hypothesis that dopamine neurons are overactive in schizophrenia.

Human diseases of the basal ganglia result in hyperkinetic or hypokinetic activity. For example, progressive familial myoclonic epilepsy (Unver-Richt-Lundberg-Lafora disease) is characterized by first generalized convulsive seizures followed by myoclonic jerks of increasing frequency and severity, and progressive dementia. Pathologic investigation reveals atypical cellular architecture in the substantia nigra. In Hallervorden-Spatz disease the patient presents a variable clinical picture that includes abnormalities of posture and muscle tone, involuntary movements and progressive dementia.

5. Retinitis Pigmentosa (RP)

Because the eye is an ectodermal derivative, that organ, like the brain, contains pigmented cells. Melanocytes are contained in the choroid, which is the structure that supports the multilayered, photosensitive retina. The outermost layer is comprised of pigmented epithelial cells. Those layers of pigmented cells absorb light that passes through the retina and minimizes interference due to reflection.

RP is an ophthalmologic disease charaoterized by progressive visual field loss and night blindness. The primary defect is at the level of the photoreceptor and pigmented cells of the retina. Currently, there is no known therapy for RP except for cases of vitamin A deficiency and removal of cataracts. Numerous low vision aids such as various magnifiers, telescopes and image intensifiers are available as supportive therapy.

C. Xeroderma Pigmentosum (XP)

XP is characterized by extreme cutaneous photosensitivity at wavelengths of 280 to 310 nm. Although dermatology textbooks often refer to the occurrence of XP in all races, there are few reports of XP in blacks. Patients sustain severe sunburns, hyperpigmented macules are prevalent and the skin becomes thickened and hyperkeratotic. Because the defect is manifest embryologically, other ectodermal derivatives are often affected. Thus, ophthalmic changes include photophobia and increased lacrimation, and neurologic abnormalities include microcephaly, retardation, deafness and ataxia. Cutaneous malignancies develop in virtually all patients with XP. Psoralens have been administered to promote a natural tan in fair-skinned patients in hopes of providing some photoprotection.

D. Melanin

For the purposes of the present description, melanins are defined below and are further described and classified as in the book entitled "Melanins," by R.A. Nicolaus, published in 1968 by Hermann, 115, Boulevard Saint-Germain, Paris, France, which work in its entirety is incorporated herein by reference. As defined by Nicolaus, melanins constitute a class of pigments which are widespread in the animal and vegetable kingdoms While the name "melanin" in Greek means black, not all melanins as pigments are black but may vary from brown to yellow.

Mammalian colors are determined chiefly by two types, eumelanins and phaeomelanins. Eumelanins are derived from the precursor tyrosine and are generally insoluble and black or brown in color. Phaeomelanins have as their precursors tyrosine and cysteine and are generally alkali-soluble and lighter in color. Allomelanins ("allo" meaning other) are formed from nitrogen-free precursors, primarily catechol and 1,8-dihydroxynaphthalene (see The Merck Index, Tenth Edition, page 827, item 5629, Melanins). Quinones are the usual intermediates in allomelanin synthesis. The synthesis of melanins occurs in nature as well as being produced synthetically. A further group of low molecular weight yellow, red and violet pigments is known as trichochromes. The trichochromes are usually classified with the melanins, since they serve as pigments and are derived from the oxidation of tyrosine.

The biosynthetic pathway by which melanin is produced is shown below as reported by Hearing, V.J. et al., *Int. J. Biochem.* 19, 1141 (1987).

E. Tyrosinase

The enzyme, tyrosinase, plays a key role in the synthesis of melanin and its derivatives. In mammals, tyrosinase is a glycosylated enzyme found in melanocytes.

It has been theorized that tyrosinase functions by means of separate catalytic sites; one site for tyrosinase hydroxylase activity, another site for dopa oxidase activity, and a third independent site for dopa as a cofactor. Hearing, V.J. et al., *Biochem. J.*, 157 549 (1976).

Tyrosinase may also play a role in catalyzing the oxidation of 5,6-dihydroxyindole to indole-5,6-quinone. Korner, A.M. et al., *Science* 217, 1163 (1982). In ViVo, mammalia tyrosinase undergoes extensive modification. When initially synthesized, tyrosinase has an apparent molecular weight of about 55,000. Glycosylation of the enzyme occurs as it is transferred through the Golgi complex and delivered to the melanocytes. Imokawa, G. et al., *J. Invest. Derm.*, 85, 165 (1985). During this modification of tyrosinase, sialic acid and 4 mol of asparagine-linked carbohydrate chains (containing mannose, glucosamine, galactose and fucose) are added to each mole of tyrosinase. Ferrini, V. et al., *Int. J. Biochem.* 19, 229 (1987). The glycosylated tyrosinase has an apparent molecular weight of about 70,000. Laskin, J.D. et al., *J. Biol. Chem.* 261, 16626 (1986).

The glycosylated tyrosinase is delivered to the melanocytes by coated vesicles. In the melanocytes, the tyrosinase is membrane bound and aggregates into a high molecular weight form. In vivo. tyrosinase is under active metabolic control involving an active degradation system which results in a biological half-like of about ten hours. Jimenez, M. et al., *Fed. Proc. Fodn. Am. Socs. Exp. Biol.* 45, 1714 (1986).

F. Tyrosinase Gene

The gene for human tyrosinase has been isolated, sequenced and cloned (PCT application WO 88/02372, published Apr. 7, 1988). The cloned gene encodes a polypeptide of 548 amino acids with a molecular weight of 62,160, excluding a hydrophobic signal peptide.

The gene for *Streptomyces glaucescens* tyrosinase has also been isolated and sequenced (Huber, M. et al., *Biochemistry* 24, 6038 (1985)). Nearly all of the codons used end in either G or C, and the overall G +C content of the gene is 71.4%. Id.

In order to isolate the *S. glaucescens* tyrosinase gene, the KpnI fragment of plasmid pMEA4 containing the *S. glaucescens* gene (Hintermann, G. et al., *Mol. Gen. Genet.* 200, 422 (1985)) is cloned into the PvuII site of pBR322 with KpnI linkers (P-L Biochemicals). Two resulting plasmids (pMEA6 and pMEA7) contain the tyrosinase gene in opposite directions. (Huber, M. et al., suora). Plasmid DNA is then isolated by conventional techniques such as those described by Maniatis, T. et al., *Molecular Cloning*, Cold Spring Harbor Laboratory, Cold Spring Harbor (1982).

Restriction endonucleases are then used according to the suppliers' instructions (Boehringer, Amsterdam) to perform digestions, and the fragments are recovered by low-melting agarose gels as described by Weislander, L., *Anal. Biochem.* 98, 305 (1979). The nucleotide sequences are then determined using the methods of Maxam, A.M. et al., *Methods. Enzyvmol.* 65, 499 (1980).

G. Melanin Concentrating Hormone

Melanin concentrating hormone (MCH) is a peptide which has been isolated from fish pituitary gland, characterized and synthesized (Kawauchi, H. et al., *Nature* 305, 321 (1983)). MCH has also been localized by immunohistochemistry in the brain and pituitary gland of salmons, frogs and rats (Baker, B.J. et al., *Gen. Como. Endocrinol.* 50, 1423 (1983), Naito, N. et al., *Neurosci. Lett.* 70, 81 (1986), Skotfitsch, G. et al., *Proc. Natl. Acad. Sci. USA* 83, 1528 (1986) and Zamir, N. et al., *Brain Research* 373, 240 (1986)).

A mammalian MCH-like substance has been recognized by salmon MCH-directed antiserum in radioimmunoassay and immunohistochemistry (Zamir, N. et al., *Proc. Natl. Acad. Sci. USA*, supra). This mammalian MCH has been diluted in parallel with synthetic MCH, but exhibits distinct chromatographic properties on both RP-HPLC and gel chromatography. Id. The persistence of this mammalian MCH in the mammalian hypothalamo-neurohypophyseal system suggests a role in posterior pituitary function, such as the regulation of food and water intake. Id.

Other functions of this mammalian MCH peptide have also been suggested. Due to the identification of MCH fibres in the human median eminence and pituitary stalk, it has been suggested that the peptide causes the aggregation or concentration of melanin in cells of the central nervous system and may be involved in the regulation of anterior pituitary function (Pelletier, G. et al., *Brain Research* 423, 247 (1987)). Furthermore, Sekiya, K. et al. in *Neuroscience* 25, 925 (1988) suggest that MCH may act as a neurotransmitter and/or neuromodulator in the central nervous system or may regulate pituitary portal-blood system and/or the neurosecretory system in mammals.

SUMMARY OF THE INVENTION

The present invention is directed to therapeutic uses of melanin, melanin precursors, melanin derivatives, melanin analogs and related substances. One particular aspect of the invention relates to the treatment of certain diseases by the administration of active substances which cause an increased melanin concentration in the patient's central nervous system (CNS). Such substances include melanin, melanin precursors, melanin derivatives, melanin analogs, melanin variants melanin-concentrating hormone (MCH), tyrosinase, tyrosinase gene and combinations thereof. These diseases include those of tissues which have lost melanin and which share a common embryological basis as the nervous system.

More specifically, the present invention is directed to the administration of melanin, a melanin precursor, a melanin variant, a melanin analog or a melanin derivative to replace lost melanin in the treatment of diseases which exhibit a decrease in the production of melanin, one or more melanin precursors or one or more derivatives or analogs of melanin and/or exhibit an increase in the catabolism or excretion of melanin, one or more melanin precursors or one or more derivative of analogs of melanin. Alternatively, the administration of MCH causes the concentration of available melanin and/or one or more melanin precursors in particular areas of the CNS, and the administration of tyrosinase or tyrosinase gene allows the patient's body to produce more melanin by increasing the conversion of assuming no precursor deficiencies melanin precursors to melanin. The present invention is especially useful for treating diseases which exhibit a neurological dysfunction or disorder. Such diseases include Parkinson's disease, Alzheimer's dsease, retinitis pigmentosa, depression, schizophrenia and other diseases such as those listed in Table 1 above. Tissues which share a common embryological basis as the nervous system include epithelium and the adrenal medulla. An example of a disease of the epithelium is xeroderma pigmentosum.

The present invention is also useful for assisting the recovery of neurons in a mammal having neuron injury by administering an effective amount of an active substance which causes an increased concentration of melanin in the neuron to aid in nerve recovery. Melanin, a melanin precursor, a melanin analog, a melanin variant or a melanin derivative can be administered to accomplish this result. Alternatively, the melanin necessary to aid nerve recovery may be concentrated in the CNS by administration of MCH, or may be produced in the patient's body by administering tyrosinase which catalyzes naturally occurring melanin precursors to melanin. Furthermore, the administration of tyrosinase gene causes the production of tyrosinase in the patient's body, thereby catalyzing the conversion of the naturally occurring melanin precursors to melanin. The present invention is further useful in protecting a mammal from a disease, such as a neurode-generative disease, or the adverse effects of toxins upon exposure to toxins such as neurodegenerative disease-causing substances, by administering an effective amount of melanin, melanin precursor, melanin derivative, melanin analog, melanin variant, MCH, tyrosinase, tyrosinase gene or a combination thereof.

A further aspect of the present invention relates to the use of melanin, a melanin precursor, a melanin derivative, a melanin analog and/or a melanin variant as a carrier for other therapeutic agents. Melanin is particularly useful as a carrier for therapeutic agents which do not easily cross the blood-brain barrier. One of the unique properties of melanins is their ability to cross the blood-brain barrier.

DETAILED DESCRIPTION OF THE INVENTION

One aspect of the present invention relates to the treatment of a mammal having a disease of a tissue which exhibits a melanin deficiency by the administration to the mammal of an effective amount of an active substance which causes an increased concentration of melanin in the effected tissue. Such active substances include but are not limited to melanin, melanin precursorsz melanin derivatives, melanin analogs, melanin variants tyrosinase, tyrosinase gene, melanin-concentrating hormone and combinations thereof. The tissue includes those which share a common embryological basis with the nervous system. The present invention is especially useful for treating such diseases which exhibit a neurological dysfunction or disorder.

The present invention is also useful for assisting the recovery of neurons in a mammal having neuron injury by administering an effective amount of the same active substance described above. The increased concentration of melanin in the affected neuron, caused by administration of the active substance aids in nerve recovery.

The present invention is further useful in protecting a patient from a disease, such as a neurodegenerative disease, or the adverse affects of toxins upon exposure to toxins, such as neurodegenerative disease-causing substances, by administering an effective amount of the active substance. The increased melanin concentration caused by administration of the active substance causes chelation or scavenging of the toxin.

The present invention still further relates to the use of melanin as a carrier for other therapeutic agents. Due to specific properties of melanin, it is particularly useful as a carrier for other therapeutic agents.

A. Definitions

In order to provide a clear and consistent understanding of the specification and claims, including the scope given to such terms, the following definitions are provided:

Administration: The application or delivery of a drug to a mammal in need of the drug. This term is intended to include any means of administration which accomplishes the application or delivery of the drug (i.e., topical, oral, aerosol, suppository, intravenous, intramuscular, injection, e.g., into the brain or the cerebrospinal fluid or other parts of the nervous system, peritoneally and the like). The term is also intended to include any means necessary to accomplish such administration, such as a sugar loading procedure to enable a drug to cross the blood-brain barrier. The term is further intended to include the in vivo production of a drug or aggregation of a drug moderated by another substance such as an enzyme (tyrosinase) or enzyme gene (tyrosinase gene) to moderate production of a drug (melanin) or its precursors, or a concentrating hormone (MCH) to moderate drug (melanin) concentration.

Blood-Brain Barrier: The blood-brain barrier is made up of brain microvessel endothelial cells characterized by tight intercellular junctions, minimal pinocytic activity, and the absence of fenestra. These characteristics endow these cells with the ability to restrict passage of most small polar blood-borne molecules (e.g., neurotransmitter catecholamines, small peptides) and macromolecules (e.g., proteins) from the cerebrovascular circulation to the brain. The blood-brain barrier contains highly active enzyme systems as well, which further enhance the already very effective protective function. It is recognized that transport of molecules to the brain is not determined solely by molecular size but by the permeabilities governed by specific chemical characteristics of the permeating substance. Thus, besides molecular size and lipophilicity, the affinity of the substances to various blood proteins, specific enzymes in the blood, or the blood-brain barrier will considerably influence the amount of the drug reaching the brain.

Common Embrvolooical Basis: This term is intended to include all tissues which are derived from the same germinal layer, specifically the ectoderm layer, which forms during the gastrulation stage of embryogenesis. Such tissues include, but are not limited to, brain, epithelium, adrenal medulla, spinal chord, retina, ganglia and the like.

Degenerative Diseases of the Nervous System: This term is intended to include any of the diseases referred to in Table 1 as well as other brain disturbances including, but not limited to, depression, dementia and schizophrenia. This term is used interchangeably with the terms "diseases with a neurological dysfunction or disorder" or "neurodegenerative diseases," which are intended to have the same meaning.

Melanin: Melanins are polymers produced by polymerization of reactive intermediates. The polymerization mechanisms include but are not limited to autoxidation, enzyme catalyzed polymerization and free radial initiated polymerization. The reactive intermediates are produced chemically or enzymatically from precursors. Suitable enzymes include, but are not limited to peroxidases and catalases, polyphenol oxidases, tyrosinases, tyrosine hydroxylases or laccases. The precursors which are connected to the reactive intermediates are hydroxylated aromatic compounds. Suitable hydroxylated aromatic compounds include, but are not limited to 1) phenols, polyphenols, aminophenols and thiophenols of aromatic or polycyclic aromatic hydrocarbons, including but not limited to phenol, tyrosine, pyrogallol, 3-aminotyrosine, thiophenol and α-naphthol; 2) phenols, polyphenols, aminophenols, and thiophenols of aromatic heterocyclic or heteropolycyclic hydrocarbons such as but not limited to 2-hydroxy-pyrrole, 4-hydroxy-1,2-pyrazole, 4-hydroxypyridine, 8-hydroxyqui and 4,5-dihydroxybenzothiazole. The term melanin includes naturally occurring melanins which are usually high molecular weight polymers (generally, molecular weights in the millions) and low molecules weight polymers as well as melanin analogs as defined below. Naturally occurring melanins include eumelanins, phaeomelanins, neuromelanins and allomelanins. The term melanin is also intended to include trichochromes when used hereafter. The term "melanin" is further intended to include both melanin, melanin analogs, melanin variants and melanin derivatives unless the context dictates otherwise.

Melanin Analog: Melanin in which a structural feature that occurs in naturally occuring or enzymatically produced melanins is replaced by an unusual substituent divergent from substituents traditionally present in melanin. An example of an unusual substituent is selinium in place of sulfur, such as selinocysteine.

Melanin Deficiency: This term is intended to refer to a condition in diseased tissue in which melanin is absent, present in a lower amount when compared to normal tissue, or functionally non-active. The deficiency may be caused by a decrease in the synthesis of melanin and/or an increase in the catabolism or excretion of melanin. The melanin may be functionally non-active as the result of a substance binding to it which destroys the melanin's activity.

Melanin Derivative: This term is intended to include any derivative of melanin which is capable of being converted in tissue to either melanin or a substance having melanin activity. An example of a melanin derivative is melanin attached to a dihydrotrigonelline carrier such as described in Bodor, N., *Ann. N. Y. Acad. Sci.* 507, 289 (1987) to enable the melanin to cross the blood-brain barrier. The term melanin derivatives is also intended to include chemical derivatives of melanin, such as an esterified melanin.

Melanin Variant: Melanin variants are defined to include various subsets of melanin substances that occur as families of related materials. Included in these subsets, but not limited thereto, are:

(1) Naturally occurring melanins produced by whole cells that vary in their chemical and physical characteristics;

(2) Enzymatically produced melanins prepared from a variety of precursor substrates under diverse reaction conditions;

(3) Melanin analogs in which a structural feature that occurs in (1) or (2) above is replaced by an unusual substituent divergent from the traditional; and (4) Melanin derivatives in which a substituent in a melanin produced in (1), (2) or (3) above is further altered by chemical or enzymatic means.

Neurodegenerative Disease-Causing Substance: Any substance which can cause a neurodegenerative disease in a mammal. Examples of such substances include N-methyl-4-phenyl-1,2,3,6-tetrahydropyridine (MPTP), 1-methyl-4-henylpyridine (MPP+) and manganese dust for Parkinson's disease; quinolinic acid for Huntington's chorea; and β-N-methylamino-L-alanine for amyotrophic lateral sclerosis, Parkinson's disease and Alzheimer's disease.

Tyrosinase: An enzyme which, in mammals, catalyzes: (a) the hydroxylation of tyrosine to dopa (3,4-dihydroxyphenylalanine); (b) the oxidation of dopa to dopaquinone; and (c) may catalyze the oxidation of 5,6-dihydroxyindole to indole-5,6-quinone. All of these reactions which are catalyzed by tyrosinase take place in the biosynthetic pathway which produces melanin. Tyrosinase is most commonly found in a glycosylated form in vivo.

B. Melanin

Naturally occurring melanins include such melanins as eumelanins, phaeomelanins, neuromelanins and allomelanins. Trichochromes which are low molecular weight polymers derived from the oxidation of tyrosine are also considered melanins for the purpose of this invention. Melanins and melanin variants are as defined above. Melanin variants are considered melanins for the purpose of this invention unless the context indicates otherwise.

Naturally occurring melanin is formed through natural biochemical pathways which involve the hydroxylation and decarboxylation of the amino acids phenylalanine and tyrosine. In one possible anabolic pathway, tyrosine is hydroxylated to form the catecholamine dopa, which is 3,4-dihydroxyphenylalanine, then the diol is oxidized to form the diketone 3,4-dioxyphenylalanine (also known as dopaquinone). The dopaquinone is cyclized to form 5,6-indolequinones, and it is the polymerization of those indolequinones that produces melanin. There are alternative pathways for melanin production. However, in each of those alternatives an understanding of the mechanisms in the final steps remains elusive.

Another pathway for natural melanin production involves the use of the neurotransmitters epinephrine (adrenaline) and norepinephrine (noradrenaline). Epinephrine is oxidized to form adrenochrome, then adrenolutin is produced and finally melanin. But melanin production is more intimately involved with the neural system because tyrosine and phenylalanine are also the precursors for the neurotransmitters epinephrine, norepinephrine and dopamine.

It is not uncommon for metabolic pathways such as these to be intimately involved, for it is a hallmark of "biological economy" that characterizes life processes. Thus, one amino acid building block such as phenylalanine can be used in a number of ways. Similarly, any one of the intermediates in a pathway such as dopamine can serve as starting material for an end product. Catabolism of the end product or intermediates ultimately produces the same building blocks for reconstruction at a later time, or produces unusable catabolites or detoxifies harmful intermediates for removal. Because those pathways are fully integrated, it is common for the end products such as melanin or epinephrine to serve as regulators for the pathway. That phenomenon is known as feedback inhibition. Thus, melanin could inhibit one of the enzymes early in the melanin biosynthetic pathway such as tyrosinase. In that way, when melanin concentration is low, tyrosinase activity is high and a large amount of tyrosine is converted into dopa for eventual production of melanin. When there is sufficient melanin, tyrosine hydroxylase activity is low and less melanin is produced. That scheme of regulatory economy is typical of metabolism, as is most noted in the endocrine system, of which the neurotransmitters are a part.

The metabolic pathway machinery for the production of products such as melanin and epinephrine from the amino acid building blocks, although likely to be present in all cells, finds maximal presence in those cells that have a high demand for those products, as in the brain. Brain cells have high levels of tyrosinase because there is high demand for dopamine, for example. The substantia nigra, that region of the brain where cells are highly pigmented because of the concentration of melanin, is noted for cells with high levels of tyrosinase. In fact, if one performs immunohistochemical analyses of brain sections using an antityrosinase antibody, the substantia nigra would be a region of the brain heavily labelled. Because of the intimate relationship between melanin and dopamine, it is not unexpected that the substantia nigra and its pigmented cells have high levels of tyrosinase.

Naturally occurring melanin can be prepared synthetically or isolated from natural sources. Natural sources include beef eyes, squid, hair, bacteria such as *Streptococcus antibioticus*, and brain, among others. Melanins can be prepared synthetically, as described by Froncisz, W. et al., *Arch.Biochem.Biophys.* 202, 289 (1980) and Lyden, A. et al., *Arch.Int.Pharmacodyn.* 259, 230 (1982), among others.

Since melanins are polymers of indole quinones, they are polar molecules with exposed amino, keto and carboxyl functionalities. The presence of these charged groups allows melanin to act as an effective ionic sponge or chelator. A variety of drugs such as chloroquine and chlorpromazine have a high affinity for melanin (Larson, B. et al., *Biochem.Pharmac.* 28, 1181 (1979)). Further, there is a high uptake by melanin of serotonin, and moderate uptake of dopamine, noradrenaline and adrenaline, while L-dopa and L-tyrosine have no affinity for melanin (Lindquist, N.G., *Acta Radiol. Suppl.* 325, 67 (1973)). As mentioned earlier, melanin also has a high affinity for the neurotoxic parkinsonism drug MPTP. High concentrations of MPTP can be found in the substantia nigra and locus cereuleus of animals and patients that have been exposed to the neurotoxin (Snyder, S.H. et al., *Neurology* 36, 250 (1986)). Melanin also readily crosses the blood-brain barrier, and is therefore useful as a carrier for other therapeutic agents which must reach brain tissue to produce their therapeutic responses.

Melanin has also been used as a chelator for uranium (Takashi, S. et al., *J.Chem.Technol.Biotechnol.* 40, 133 (1987)) and as a sorbent for clarifying and stabilizing wine (USSR 924,098).

Melanin has additional anti-toxin characteristics as a free radical scavenger or oxygen scavenger, and as such can serve as a terminator of free radical chain reactions. As a free radical scavenger, melanin may play an important role in preserving cells from the toxic effects of $O_2$. Geremia, C. et al., *Comp. Biochem. Physiol.* 79B, 67 (1984).

Melanin has many other interesting properties such as ultraviolet absorption, which has been utilized to prepare optical lenses (U.S. Pat. No. 4,698,374) as well as cosmetic creams (Jap. 49-071149). Melanin has both semiconductor (Culp, C.J. et al., *J.Appl.Phys.* 46, 3658 (1975)) and superconductor (Cope, F.W., *Physiol.Chem. Phys.* 10, 233 (1978)) properties.

Melanin variants have all of the above-described properties of naturally occurring melanins, but in addition, melanin analogs cause an increase in the permeability of the blood-brain barrier. The mechanism for this increased permeability of the blood-brain barrier is not known.

Due to their ability to increase the permeability of the blood-brain barrier, the melanin variants are also useful as carriers for other therapeutic agents. Two examples of such therapeutic agents which will cross the blood-brain barrier when linked to melanin are boron and nerve growth factor.

Irradiated boron has a very high energy for a very short distance, and is therefore selectively lethal to cells in its immediate vicinity. For this reason, boron has been used in neutron capture therapy of cancerous cells.

Neutron capture therapy entails the delivery of the boron-10 isotope to cancerous areas of the body, and subsequent irradiation of the boron-10 isotope. Boron-10 readily absorbs thermal neutrons (slow neutrons) and the activated nucleus rapidly decays to lithium 7 and an alpha particle. The alpha particles are cytotoxic, so they kill the cancerous cells surrounding the boron and thus, cause tumor reduction. The boron which is used for neutron capture therapy should have at least a 20% natural abundance of the boron-10 isotope.

The boron may be carried to the cancerous site by a variety of vehicles. Conventional vehicles include steroids, antibodies, nucleosides, chlorpromazine, thiouracil, amino acids, porphyrins and liposomes, Fairfield et al., *Int. J. Radiation Oncology Biol. Phys.* 11, 831 (1985). It has now been found that melanin (including melanin variants) is also an effective vehicle for the transport of boron to cancerous sites in the body.

Melanin binds boron very strongly, and is therefore an excellent vehicle for the boron when combined with an antibody specific to the cancerous cells. As noted in U.S. Pat. No. 4,824,659, there has been a need for a more efficient method to conjugate boron-10 and antibody, and melanin provides that efficient method. The antibody directs the boron/melanin complex to the specific cancerous site where the boron-10 is irradiated with slow neutrons.

A preferred source of slow neutrons for irradiation of the boron-10 isotope is a 2 keV beam. The amount of boron atoms necessary in the cancerous tissue for effective neutron capture therapy is generally quantified as a molar concetration which is about $10^4$ to $10^6$ higher than that needed for diagnostic techniques (Fairchild et al., supra).

The therapeutic efficacy of neutron capture therapy is generally dependent on the ratio of tumor dose of boron to maximum normal tissue dose of boron. This ratio is termed the "advantage factor", and should be greater than 1. Id. The higher the advantage factor is above 1, the more efficacious is the neutron capture therapy. It is generally difficult to achieve an advantage factor significantly greater than 1 because the treatment volumes must be extended beyond the bulk tumor in order to include unseen microscopic extensions of the tumor growth. The presence of normal tissues within this extended treatment volume then limits the tumor dose to the normal-tissue tolerance dose.

An additional advantage of using melanin as the vehicle to transport boron to a tumor site is the ability of melanin to cross the blood-brain barrier, and melanin analog's activity which causes an increase in the permeability of the blood-brain barrier. These properties of melanin permit easier treatment of brain tumors than is possible with the conventional boron vehicles which do not easily cross the blood-brain barrier and do not increase the permeability of the blood-brain barrier.

In addition to being an excellent carrier or vehicle for boron, melanin has also been found to be a very useful carrier for nerve growth factor. Like boron, nerve growth factor binds strongly to melanin. The major advantage of using melanin as a carrier for nerve growth factor in the ability to get nerve growth factor across the blood-brain barrier.

As discussed above, not only does melanin easily cross the blood-brain barrier, but the melanin variants also increase the permeability of the blood-brain barrier. Due to the substantial amount of nerve tissue in the brain, the ability to easily transport nerve growth factor across the blood-brain barrier is a major improvement over conventional nerve growth factor therapy. This major improvement over conventional the nerve growth factor therapy is attributable to the use of melanin as a carrier for the therapeutic agent.

C. Neurodegenerative Disease Effects on Melanin-Containing Cells

In order to develop therapy programs for any disease, it is useful to identify (a) potential causes of the disease, in an attempt to avoid them; (b) potential manifestations of the disease, in an attempt to identify aspects of the disease which may be treated, and (c) drugs which are similar to known therapeutic drugs. Little is known as to the cause-and-effect relationship in the neurodegenerative diseases. One problem in these diseases is that few animal models exist which can be utilized to gain the necessary understanding of each disease and its treatment.

Post-mortem examination of the brain shows a generalized atrophy. There are extensive histologic changes in Alzheimer's disease (AD) dominated by the presence of intracellular amyloid plaques and neurofibrillary tangles. Plaques and tangles are rare, however, in the basal ganglia and substantia nigra. Many specimens from AD patients demonstrate a loss of pigmentation in the area of the locus ceruleus, which is a major source of noradrenergic synthesis in the brain.

Dopaminogenic neuronal activity may be abnormal in cases of schizophrenia. There is a reduction in fresh volume of substantia nigra in brains of schizophrenics with the majority of that due to a reduction of cell body volume in the medial portions of that region. Nevertheless, the reduction by cells is not as contributory to the fresh volume loss as is reduction of the neuropil. It is unknown whether those observations have a bearing on the hypothesis that dopamine neurons are overactive in schizophrenia.

Human diseases of the basal ganglia result in hyperkinetic or hypokinetic activity. For example, progressive familial myoclonic epilepsy (Unver-Richt-Lundberg-Lafora disease) is characterized by first generalized convulsive seizures followed by myoclonic jerks of increasing frequency and severity, and progressive dementia. Pathologic investigation reveals atypical cellular architecture in the substantia nigra. In Hallervorden-Spatz disease the patient presents a variable clinical picture that includes abnormalities of posture and muscle tone, involuntary movements and progressive dementia.

Retinitis pigmentosa is an ophthalmologic disease characterized by progressive visual field loss and night blindness. The primary defect is at the level of the photoreceptor and pigmented cells of the retina. Currently, there is no known therapy for retinitis pigmentosa except for cases of vitamin A deficiency and removal of cataracts. Numerous low-vision aids such as various magnifiers, telescopes and image intensifiers are available as supportive therapy.

Probably the most studied disease in terms of brain pathology has been Parkinson's disease. It is well known that substantial changes occur within the substantia nigra of patients suffering from Parkinsonism. As previously discussed, the substantia nigra is one of the most heavily pigmented areas of the brain and consequently contains significant amounts of melanin. It has been demonstrated that cell death in the substantia nigra in Parkinson's disease is related to a loss of melanin in the neurons of the substantia nigra (Mann et al., supra; Hirsch, E. et al., Nature 334, 345 (1988)). Furthermore, it has been established that MPTP, which can cause Parkinson's disease, binds to neuromelanin (D'Amato et al. (1986), suora) and is concentrated in the substantia nigra and locus cereuleus (Snyder et al., supra).

The common factor in each of these diseases is that a tissue which is highly pigmented, i.e., one which contains melanin, is involved in the disease. In almost every instance, there is a decreased melanin content, i.e., a loss of pigment, which may lead to cell death. As described further below, applicant has discovered that treatment of neurodegenerative diseases with melanin can ameliorate the primary neurological symptoms of the disease.

D. Asoects of the Invention

In its broadest aspects, therapeutic uses of melanin include: 1) melanin as a drug, 2) melanin as a drug delivery agent and 3) melanin as a target for various types of radiation. In instances in which selected delivery or target cell sequestration is not required native melanin as well as melanin variants, melanin analog and melanin derivatives can be used. Melanins, melanin variants, melanin analogues, and melanin derivatives can be produced with predictable molecular weights, particle sizes, and compositions. Consequently, melanins can now be attached to antibodies and thus targeted for specific cell (e.g. liver cells).

Melanin has a number of properties which can be exploited to both alter cellular metabolism and/or remove intra- and intercellular toxins. Such properties include, oxygen and free radical scavenging, metal binding, binding of organic cationic species (MPP+ is one example), catalysis of coupled redox reactions. These properties are notinterdependent, and, melanin can be selectively altered and optimized.

Drugs can be covalently bound to melanin or just adsorbed on its surface. They can be attached in such a manner that induced cellular metabolism at the target cell would cause release of the therapeutic agent. The melanin derivatives are preferred for this type of application.

Melanin absorbs various types of radiation as well as being capable of binding boron. Melanin can be used to absorb ultraviolet rays in skin creams as well as to translate irradiation to cover tissue. Each of these broad aspects is further described below.

1. Therapy

One aspect of the present invention is that an active substance such as melanin can be used to treat neurodegenerative diseases or diseases of tissues which share a common embryological basis with the nervous system. As discussed above, the loss of melanin can be seen in many neurodegenerative diseases. For example, the retina suffers a loss of pigmented cells in retinitis pigmentosa. In Alzheimer's disease there is a generalized atrophy and a loss of pigment, i.e., melanin, in the area of the locus ceruleus, which is a major source of noradrenergic synthesis in the brain. A reduction in fresh volume of the substantia nigra, especially of the neurophil, has been seen in schizophrenics. A typical cellular architecture also exists in Unver-Richt-Lundberg-Lafora disease.

Probably the most studied disease in terms of brain pathology has been Parkinson's disease. It is well known that substantial changes occur within the substantia nigra of patients suffering from Parkinsonism. As previously discussed, the substantia nigra is one of the most heavily pigmented areas of the brain and consequently contains significant amounts of melanin. It has been demonstrated that cell death in the substantia nigra in Parkinson's disease is related to a loss of melanin in the neurons of the substantia nigra (Mann et al., suora: Hirsch, E. et al., Nature 334, 345 (1988)). Furthermore, it has been established that MPTP, which can cause Parkinson's disease, binds to neuromelanin (D'Amato et al. (1986), suora) and is concentrated in the substantia nigra and locus cereuleus (Snyder et al., suora).

It has now been found that the administration of melanin to a mammal having a disease of tissue which exhibits a melanin deficiency, such as the neurodegenerative diseases discussed above, is capable of ameliorating the primary neurological symptoms of the neurodegenerative disease which is treated. Similar improvement in overall functional ability is also improved. Furthermore, secondary motor manifestations of the neurodegenerative diseases are also proportionately improved upon administration of melanin. The melanin can be administered by any means which will insure that it reaches the desired tissue. In many instances, the administration may require mechanisms for crossing the blood-brain barrier. Several mechanisms are described below and others are known in the art.

Since the treatment of the disease will require many separate doses of melanin, some mechanisms will be more preferred than others. Suitable doses for this purpose are from about 0.5 to about 150 mg/kg/day and preferably from about 1 to about 50 mg/kg/day of the active ingredient. Proper doses are determined as described below.

Melanin can also be used for ameliorating Alzheimer's disease since it is capable of aiding the recovery of injured neurons (discussed in further detail below). Suitable doses for this purpose are as described above, and the optimal dose is determined as described below.

An alternative method for treating these nervous system diseases with melanin is to enhance the in vivo production of melanin by administering tyrosinase to the effected patient. Tyrosinase catalyzes at least two, and possibly three, of the reactions in the biosynthetic pathway which produces melanin.

Naturally, occurring tyrosine in the human body is hydroxylated to 3,4-dihydroxyphenylalanine (dopa), and the hydroxylation is catalyzed by tyrosinase. Tyrosinase also catalyzes the subsequent oxidation of dopa to dopaquinone. The dopaquinone is a precursor for two separate biosynthetic pathways for the production of melanin. Therefore, both tyrosinase-catalyzed reactions which lead to the production of dopaquinone (the hydroxylation of tyrosine to dopa and the oxidation of dopa to dopaquinone) are important reactions in the human body's production of melanin.

One pathway from dopaquinone to melanin involves a ring closure and hydrogenation of dopaquinone to produce leucodopachrome. This is followed by partial oxidation of leucodopachrome to dopachrome, and decarboxylation and hydroxylation of the dopachrome to 5,6-dihydroxy-indole. The 5,6-dihydroxyindole is then oxidized to indole-5,6-quinone, and it is at this step that tyrosinase is again believed to serve as a catalyst. Korner, A.M. et al., *Science* 217, 1163 (1982). Tyrosinase is believed to catalyze this oxidation reaction. The indole-5,6-quinone is then converted to melanin or eumelanin.

The other pathway from dopaquinone to melanin involves the addition of cysteine to dopaquinone to produce 5-S-cysteinyldopa, followed by the oxidation of 5-S-cysteinyldopa to 5-S-cysteinyldopaquinone. A ring closure of the 5-S-cysteinyldopaquinone then yields 7-alanyl-5-hydroxy-3-carboxy-2H-1,4-benzothiazine which is subsequently decarboxylated to yield 7-alanyl-5-hydroxy-2H-1,4-benzothiazine. At this point, the 7-alanyl-5-hydroxy-2H-1,4-benzothiazine is converted to melanin and pheomelanin. Tyrosinase does not play any additional role in this melanin production pathway.

It has now been found that the administration of tyrosinase to a mammal having a disease of a tissue which exhibits a melanin deficiency, such as the neurodegenerative diseases discussed above, is capable of ameliorating the primary neurological symptoms of the neurodegenerative disease which is treated. Similar improvement in overall functional ability is also improved. Furthermore, secondary motor manifestations of the neurodegenerative diseases are also proportionately improved upon administration of tyrosinase. These improvements are believed to be due to the increased in vivo production of melanin brought about by the increased tyrosinase-mediated catalysis of reactions along the biosynthetic pathway responsible for the production of melanin.

The tyrosinase can be administered by any means which will insure that it reaches the desired tissue. In many instances, the administration will require mechanisms for crossing the blood-brain barrier. Several mechanisms are described below and others are known in the art. Since the treatment of the disease will require many separate doses of tyrosinase, some mechanisms will be more preferred than others. The amount of tyrosinase administered must be sufficient to catalyze the melanin-producing reactions such that sufficient melanin is produced to alleviate the disease symptoms. Proper doses are determined as described below.

Tyrosinase can also be used for ameliorating the symptoms of Alzheimer's disease since it increases the production of melanin in vivo, and melanin is capable of aiding the recovery of injured neurons (discussed in further detail below). Suitable doses for this purpose are as described above, and the optimal dose is determined as described below.

Another method by which the in vivo production of melanin may be enhanced is by the administration of the tyrosinase gene to the effected patient. After administration, the tyrosinase gene transfects susceptible mammalian cells and tyrosinase is produced. The tyrosinase, in turn, catalyzes the production of melanin from naturally occurring melanin precursors as explained above.

The most common method by which tyrosinase gene is introduced into the mammalian system is by its incorporation into a defective herpes simplex virus 1 (HSV-1) vector. Particularly, the defective HSV-1 vector, pHSVlac, developed by Geller et al., *Science* 241, 1667 (1988) is especially useful for this purpose. This vector is useful for transneuronally transporting genes from peripheral neurons to the primary target cells in the brain (Ugolini et al., *Science* 243, 89 (1989)). The amount of tyrosinase gene administered must be sufficient to transfect susceptible mammalian cells so that tyrosinase is produced therefrom.

A further method of treating the melanin deficiency diseases is to increase the concentration of naturally occurring melanin at the target cells in the central nervous system by the administration of melanin-concentrating hormone (MCH). Commonly, a combination of MCH and tyrosinase or tyrosinase gene is administered as an effective combination for the treatment of melanin deficiency diseases. The tyrosinase or tyrosinase gene causes an increased melanin production, and the MCH induces the aggregation of melanin in the target cells and tissues.

2. Prophylaxis

A second aspect of the present invention is that an active substance such as melanin can be used to prevent degenerative diseases of the nervous system which are caused by exposure of a mammal to toxic agents which cause such neurodegenerative diseases. Toxic agents which are known to cause neurodegenerative diseases include N-methyl-4-phenyl-1,2,3,6-tetrahydropyridine (MPTP) and 1-methyl-4-phenylpyridine (MPP+) and manganese dust for Parkinson's disease; quinolinic acid for Huntington's chorea; $\beta$-N-methylamino-L-alanine for amyotrophic lateral sclerosis, Parkinson's disease and Alzheimer's disease; and aluminum has been implicated in Alzheimer's disease. In addition to these agents, the toxic metabolite of MPTP, MPP+, has been field-tested as a herbicide under the name Cyperquat. The well-known herbicide Paraquat chemically resembles MPP+. Cyperquat and Paraquat are pyridine derivatives. Many analogs of MPTP exist in the environment and could also be involved in idiopathic parkinsonism. One of the MPTP analogs, 4-phenylpyridine, a constituent of peppermint and spearmint tea, was toxic to catecholamine neurons in vitro (Snyder et al., suora). Melanin can also be used to prevent the adverse effects caused by toxins which are absorbed, inhaled or ingested by a mammal. In addition to the toxins discussed above, other toxins include, but are not limited to, metals, metal-containing compounds, radioisotopes and radioactive compounds, including radioactively labelled therapeutics and diagnostics. Metals include, but are not limited to, aluminum, lead and manganese. Melanin is especially useful as a chelating agent to lower or eliminate aluminum agents.

Melanin has been found to be able to bind MPTP as well as MPP+. Administration of melanin can thus effectively bind MPTP, MPP+ and other neurodegenerative disease-causing substances before the substances reach the tissue (especially brain tissue) they damage. The melanin can be administered by any means, but for present purposes it is preferred to administer it orally, by inhalation or suppositories. Suitable doses for this purpose are from about 0.5 to about 100 mg/kg, and preferably from about 1 to about 5 mg/kg of the active ingredient. This aspect of the invention is shown in Examples 1 and 2 below.

Alternatively, the administration of tyrosinase can increase the production of melanin in vivo. thereby causing the binding of neurodegenerative disease-causing substances before the substances reach the tissue (especially brain tissue) which they damage. The tyrosinase can be administered by any means, but for present purposes it is preferred to administer it orally, by inhalation or by suppositories. As in the case of treating melanin deficiency diseases, the amount of tyrosinase administered must be sufficient to catalyze the melanin producing reactions such that sufficient melanin is produced to alleviate the disease symptoms.

As is also the case with treatment of melanin deficiency diseases, another method by which the in vivo production of melanin may be enhanced us by the administration of the tyrosinase gene to the effected patient. After administration, the tyrosinase gene transfects susceptible mammalian cells and tyrosinase is produced. The tyrosinase, in turn, catalyzes the production of melanin from naturally occurring melanin precursors as explained above.

The most common method by which tyrosinase gene is introduced into the mammalian system is by its incorporation into a defective herpes simplex virus 1 (HSV-1) vector. Particularly, the defective HSV-1 vector, pHSVlac, developed by Geller et al., *Science* 241, 1667 (1988) is especially useful for this purpose as explained above. The amount of tyrosinase gene administered must be sufficient to transfect susceptible mammalian cells so that tyrosinase is produced therefrom.

Tyrosinase gene may also be introduced into the mammalian system using DNA contructs for retrovirus packaging cell lines as described in U.S. Pat. No. 4,861,719 incorporated herein by reference. Briefly, a cell line containing a DNA construct such as pPAM3 (ATCC No. 40234) is used to transmit high titers of retroviral vectors which carry tyrosinase gene. An example of such a cell line is PA317 (ATCC No. CLR 9078).

Useful DNA constructs such as pPAM3 are constructed by deleting all of the cis-acting elements except for the tRNA binding site from the genome of a replication-competent retrovirus. The particular cis-acting elements which are deleted are: the packaging signal; the site for initiation of second strand DNA synthesis; the site required for translation of reverse transcriptase during first strand DNA synthesis; and the provirus integration signal.

The retrovirus vectors produced by PA317 cells are capable of infecting a variety of hosts including mouse, rat, cat, dog and human cells. Hemopoietic progenitor cells from human bone marrow and mouse embryo cells have been infected by retroviral vectors secreted from PA317 cells. The vector titer from the PA317 cells is very high (up to $10^7$ colony forming units/ml), and therefore, these cells are useful in mammalian gene therapy.

A further method of prophylaxis against the melanin deficiency diseases is to increase the concentration of naturally occurring melanin at the target cells in the central nervous system by the administration of melanin-concentrating hormone (MCH). Commonly, a combination of MCH and tyrosinase or tyrosinase gene is administered as an effective combination for the treatment of melanin deficiency diseases. The tyrosinase or tyrosinase gene causes an increased melanin production, and the MCH induces the aggregation of melanin in the target cells and tissues.

3. Neuron Recovery

Another aspect of the present invention is that an active substance such as melanin can be used to assist in the recovery of injured neurons. The neurons could be injured as a result of direct injury or disease. For example, it is known that MPTP destroys a substantial number of dopaminergic nerve terminals in the striatum of young mature mice, and that after five months there is a substantial, though incomplete, recovery of striated dopamine nerve terminal markers. Ricourte, G.A. et al., *Brain Res.* 376, 117 (1986). It is also known that melanin is present in all neurons in the form of dark, irregularly shaped granules called Nissl bodies. Nissl bodies are scattered throughout the cytoplasm and occur in dendrites of the larger neurons. They appear to be absent in the axon and axon-hillock. In pathological conditions, there is a partial or complete reduction in the amount of Nissl bodies. For example, it is known that Nissl bodies disappear with nerve injury but reappear upon nerve recovery. Within certain regions of the brain, there are areas of neurons that have high concentrations of Nissl bodies, thereby rendering localized regions black. Examples of these areas include the substantia nigra and locus ceruleus. It is known that Nissl bodies disappear with nerve injury but reappear upon nerve recovery. It has been found that the administration of melanin or a melanin derivative is able to aid in the recovery of neurons by accelerating the time frame for neuron recovery. This aspect of the invention is shown in Example 3 below.

It has also been found that the administration of tyrosinase, tyrosinase gene, MCH or combinations thereof aid in the recovery of neurons. The tyrosinase increases the production of melanin in vivo. and the melanin accelerates the time frame for neuron recovery. The administration of tyrosinase gene and/or MCH aids in neuron recovery by promoting the same reactions described above for treatment and prophylaxis of melanin deficiency diseases.

Melanin can also aid neuron recovery by acting as a carrier for nerve growth factor (NGF). NGF was originally derived from mouse sarcomas, moccasin snake venom and mouse salivary glands as a non-dialyzable, heat-labile protein molecule with a molecular weight of about 20,000 or about 44,000 (Levi-Montalcini, *Science* 237, 1154 (1987)). NGF is essential in the early differentiation stages of its target cells as evidenced by failure of chick embryo nerve cells to survive in vitro in the absence of the daily addition of nanogram quantities of NGF to the culture medium (Levi-Montalcini et al., *Dev. Biol.* 7, 653 (1963)).

NGF is a dimer of two identical subunits held together by noncovalent bonds. Although it is as yet unknown whether each NGF subunit is biologically active, it has been demonstrated that a covalently cross-linked form of the dimer maintains full activity (Stach et al., *J. Biol. Chem.* 249, 6668 (1974)).

NGF is taken up by nerves endings of the sympathetic or sensory fibers, and is retrogradely transported to the cell perikarya. Specifically, NGF is a trophic messenger conveyed through nerve fibers from peripheral cells to the invigorating neurons (Stdckel et al., *Brain Res.* 76, 413 (1974); Hamburger et al., *J. Neurosci.* 1, 60 (1981)). NGF has the ability to direct growing or regenerating axons of sensory and sympathetic fibers along its concentration gradient (neurotropism) (Gundersen et al., *Science* 206, 1079 (1979)).

Both small and large neuronal populations located in different brain areas have been shown to exhibit all of the properties and responses typical of sensory and sympathetic cells such as: 1) presence of specific receptors (Szutovitz et al., *J. Biol. Chem.* 251, 1516 (1976)); 2) retrograde transport of NGF (Seiler et al., *Brain Res.* 30, 23 (1984)); 3) increased neurotransmitter synthesis, particularly acetylcholine (Gnahn et al., *Dev. Brain Res.* 9, 45 (1983), Hefti et al., *Brain Res.* 293, 305 (1984), Mobley et al., *Science* 229, 284 (1985)); and 4) trophic response manifested as protection against exogenous NGF administration to selective noxious treatments or surgical transactions otherwise leading to cell death (Williams et al., *Proc. Natl. Acad. Sci U.S.A.* 83, 9231 (1986), Kromer, *Science* 235, 214 (1987)).

NGF target cells include neural crest derivatives such as sympathoadrenal cells and sensory neurons. Exemplary sympathoadrenal cells include long sympathetic neurons, short sympathetic neurons, paraganglia cells, small intensely fluorescent (SIF) cells, and normal and neoplastic chromaffin cells. Additional NGF target cells include those of the central nervous system such as cholinergic neurons and adrenergic, indoleaminergic and peptidergic neurons. Some cells of nonneuronal origin such as mast cells are also targets for NGF.

There has been found a high degree of homology in the cloned NGF gene of mice (Scott et al., *Nature* 302, 538 (1983)), humans (Ulbrich et al., *Nature* 303, 821 (1983)), bovine (Meier et al., *EMBO J.* 5, 1489 (1986) and chickens (Ebendal et al., *EMBO J.* 5, 1483 (1986)). The human NGF gene is located on the proximal short arm of chromosome 1, and codes for a large polypeptide of 307 amino acids (Francke et al., *Science* 222, 1248 (1983)).

One method for producing NGF is taught by Rosenberg et al., *Science* 242, 1575 (1988), and involves a retroviral vector constructed from Maloney murine leukemia virus (Wolf et al., *Mol. Biol. Med.* 5, 43 (1988), Varmus et al., *RNA Tumor Viruses*, R. Weiss, N. Teich, H. Varmus, J. Coffin, Eds. (Cold Spring Harbor Press, Cold Spring Harbor, N.Y., 1982) pp. 233-249). The vector contains the 777- bp HgA I-Pst I fragment of mouse NGF cDNA under control of the viral 5' long terminal repeat. The NGF cDNA fragment was prepared in accordance with the techniques taught by Scott et al., *Nature* 302, 538 (1983) and Ulbrich et al., *Nature* 303, 821 (1983). The vector also contains a dominant selectable marker encoding the neomycin-resistance function of transposon Tn5 under control of an internal Rous sarcoma virus promoter.

Transmissible retrovirus is produced by transfecting vector DNA into PA137 amphotrophic producer cells (Miller et al., *Mol. Cell Biol.* 6, 2895 (1986)) by the calcium phosphate co-precipitation method (Graham et al., *Virology* 52, 456 (1973)) and by using medium from these cells to infect Ψ2 ecotropic producer cells (Mann et al., *Cell* 33, 153 (1983)) in the presence of Polybrene (Sigma; 4 μg/ml). Virus from the Ψ2 clone producing the highest titer is used to infect an established rat fibroblast cell line 208F (Quade, *Virology* 98, 461 (1979)) as described by Miyanohara et al., *Proc. Natl. Acad. Sci. U.S.A.* 85, 6538 (1988).

Individual neomycin-resistant colonies, selected in medium containing the neomycin analog G418, are expanded and tested for NGF production and secretion by a two-site enzyme immunoassay, with commercially available reagents according to the manufacturer's protocols (Boehringer Mannheim). The NGF secreted by the clones is biologically active as determined by its ability to induce neurite outgrowth from PC12 rat pheochromocytoma cells (Greene et al., *Proc. Natl. Acad. Sci. U.S.A.* 73, 2424 (1976); Greene, *Brain Res.* 133, 350 (1977)).

Melanin readily binds nerve growth factor, and therefore can transport the nerve growth factor across the blood-brain barrier. The brain is an organ rich in nervous tissue, and therefore an organ where nerve growth factor is particularly useful. By transporting nerve growth factor across the blood-brain barrier and/or increasing the permeability of the blood-brain barrier, melanin is useful in allowing nerve growth factor to reach tissue where it is particularly useful and would not otherwise be capable of easily reaching.

4. Melanin As A Carrier For Other Therapeutic Agents

An additional aspect of melanin therapy is the use of melanin as a carrier for other therapeutic agents. Two therapeutic agents with which melanin is especially useful as a carrier are boron and nerve growth factor. However, melanin is also useful as a carrier with any other agent which binds to melanin.

Boron is particularly useful in the treatment of cancerous tumors with neutron capture therapy (thermal neutron activated radiotherapy). As explained above, boron-10 isotopes which have been irradiated by slow neutrons, release significant amounts of radiation in their immediate vicinity. By targeting boron to cancerous and/or tumorous areas, the radiation emitted from the boron-10 isotopes is selectively lethal to the cancerous cells in the immediate vicinity of the boron.

Melanin has been found to be a very useful carrier for boron. The boron is strongly bound by melanin, and the boron/melanin complex thus created can be attached to an antibody so that the complex is delivered to a specific cancerous site. As noted in U.S. Pat. No. 4,824,659, an antibody conjugate must have a sufficiently large number of boron atoms in order to function as an efficient therapeutic agent. The strong binding of boron to melanin allows the described antibody conjugates to have sufficient boron atoms to be efficient therapeutic agents.

Melanin is particularly useful as a boron carrier when the cancerous cells to be treated are located in the brain. The binding of boron to melanin permits relatively easy transport of boron across the blood-brain barrier. Melanin facilitates the boron transport cross the blood brain barrier in two ways: 1) melanin itself easily crosses the blood-brain barrier; and 2) melanin analog causes an increase in the permeability of the blood-brain barrier.

The antibodies conjugated to the melanin/boron complex may be any type of immunoglobulin molecule having a region which specifically binds to an antigen of therapeutic interest. These immunoglobulin molecules include whole immunoglobulins such as IgA, IgD, IgE, IgG, IgM and the like, or immunoglobulin fragments such as Fab, Fab', F(ab)$_1$, F(ab')$_2$ and the like. Useful antibodies also include hybrid antibodies or hybrid antibody fragments.

In addition to being a useful carrier for boron, melanin is also a useful carrier for nerve growth factor. Like boron, nerve growth factor binds strongly to melanin.

As discussed in detail above, nerve growth factor is a non-dialyzable, heat-labile protein molecule with a molecular weight of about 20,000 or about 44,000 (Levi-Montalcini, *Science* 237, 1154 (1987)). The NGF molecule is a dimer of two identical subunits held together by noncovalent bonds. NGF target cells include neural crest derivatives which include sympathoadrenal cells and sensory neurons. NGF has the ability to direct growing or regenerating axons of sensory and sympathetic fibers along its concentration gradient (Gundersen et al., *Science* 206, 1079 (1979)).

When bound to melanin, NGF can relatively easily cross the blood-brain barrier, because of melanin's ability to cross the blood-brain barrier and melanin analog's ability to increase the permeability of the blood-brain barrier. The brain is an area of particular usefulness for NGF due to the large amount of nerve tissue present in this organ. The use of melanin as a carrier for NGF aids the transport of this therapeutic agent to an area where it is particularly useful, and would not easily reach otherwise.

E. Pharmaceutical Compositions and Delivery

Pharmaceutical compositions containing the active substance of the present invention (i.e. melanin, melanin derivatives, tyrosinase, tyrosinase gene, MCH and combinations thereof) in intimate admixture with a pharmaceutical carrier can be prepared according to conventional pharmaceutical compounding techniques. The carrier may take a wide variety of forms depending on the form of preparation desired for administration, e.g., intravenous, oral, topical, aerosol, suppository, parenteral or spinal injection. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents, pH adjusting agents, isotonicity adjusting agents and the like may be employed. For topical administration, the carrier may take a wide variety of forms depending on the form of preparation, such as creams, dressings, gels, lotions, ointments or liquids. Aerosols are prepared by dissolving or suspending the active ingredient in a propellant such as ethyl alcohol or in propellant and solvent phase. Suppositories are prepared by mixing the active ingredient with a lipid vehicle such as theobroma oil, cacao butter, glycerin, gelatin, or polyoxyethylene glycols. The pharmaceutical compositions for topical or aerosol form will generally contain from about 1% by weight to about 40% by weight, depending on the particular form employed.

Melanin, whether used as a therapeutic agent or as the carrier for another therapeutic agent is soluble in aqueous solution. Particularly, melanin is soluble in aqueous solutions of pH 5 or higher, and preferably, aqueous solutions of pH 8 or higher.

There are unique considerations in the treatment of central nervous system dysfunction. Unlike other tissues, brain tissue is not redundant. It is highly differentiated, compartmentalized, and cannot be replaced. Thus, neuropharmaceutics must be found nontoxic to normal tissue. The real problem, however, has been to find the most efficacious route of circumventing the blood-brain barrier. Although melanin has been found to be capable of crossing the blood-brain barrier, other devices or methods for transport across the blood-brain barrier can even further enhance melanin's ability to cross the blood-brain barrier.

One way to bypass the barrier is by intracerebrospinal fluid administration by lumbar puncture or by the intraventricular route. Catheterization using the Ommaya reservoir is used, but logistics dictate that to be a last-resort method.

Because the barrier is selective, some drugs can be administered orally. Certain lipophilic chemicals or agents that mimic the neural amino acids can bypass the barrier by mere diffusion or by transport via the energy dependent membrane-bound carrier, respectively. Melanin derivatives can be prepared to add lipid and/or carbohydrate groups to the melanin to make it more lipophilic and hence enhance its ability to cross the blood-brain barrier.

An example of a drug administered intrathecally is methotrexate, an antineoplastic agent, in the treatment of meningeal leukemia. The sodium salt of methotrexate is administered in solution in doses of 12 mg per square meter of body surface or in an empirical dose of 15 mg. The drug is given ever two to five days until the cell count of the cerebrospinal fluid returns to normal. L-dopa can be used to compensate for the depletion of dopamine that occurs in parkinsonism because it also passes freely through the blood-brain barrier.

Transient reversible modification of the blood-brain barrier is accomplished in either of two ways—osmotic opening or metrazol opening. The first method is based on increasing capillary permeability by osmotically-induced shrinkage of the endothelial cells which caused widening of the intercellular tight junctions. The osmotic load is generally a hyperosmotic water-soluble agent such as mannitol or arabinose. Briefly, under general anesthesia, a transfemoral catheter is introduced into the internal carotid or vertebral artery and 150-300 ml infusion of 25% mannitol is administered at 6-10 mg/sec for 30 seconds. The intravenous infusion of melanin or tyrosinase is begun approximately five to seven minutes before the mannitol infusion and is continued for 15 minutes. The transfemoral catheter is removed and the patient observed for 24-48 hours.

Alternatively, the active agent (melanin or tyrosinase) may be linked to the osmotic agent (mannitol, arabinose, glucose or other sugar moiety), and a single infusion may be used. Conventional techniques may be used to link the active agent and the osmotic agent. The linked agent itself will then cause the osmotically-induced shrinkage of the endothelial cells in order to widen the tight intercellular junctions. The linked agent may be designed such that the active agent (melanin or tyrosinase) is cleaved from the linked agent after the blood brain barrier has been crossed.

In the second method, capillary permeability is increased by eliciting seizure activity using a central nervous stimulant such as pentylenetetrazol. The technique is similar to that of osmotic opening with the replacement of mannitol infusion by parental delivery of the stimulant.

A drug also can be disguised so that is able to cross the blood-brain barrier. One method of accomplishing the disguise is to prepare a redox system as described by Bodor, supra. In this system a derivative of the drug is prepared which is capable of crossing the blood-brain carrier and which is converted in tissue to the drug or to a substance having the activity of the drug. In the case of melanin or tyrosinase, a derivative is prepared by attaching melanin or tyrosinase to a dihydrotrigonelline carrier such as described in Bodor, supra.

A similar method of disguising a drug so that it will cross the blood brain barrier is to create a redox system in which the drug is coupled to a pyridinium carrier as described by Bodor, N. et al., *Pharmac. Ther.* 19, 337 (1986). Commonly used pyridinium carriers include substituted nicotinic acid and nicotinamide. After coupling, the drug-carrier complex is reduced, yielding a dihydropyridine. The reduced complex is then administered systemically. The reduced complex will cross the blood brain barrier due to its enhanced membrane permeability, and it will also be distributed elsewhere in the body.

At all locations in the body (in the brain as well as elsewhere in the body) the reduced drug-carrier complex will be subject to oxidation. However, the rate of oxidation can be controlled to some extent by selected substitution of the pyridine ring. Following oxidation, the charged drug-carrier complex is rapidly eliminated from the peripheral blood system by renal and/or biliary processes. However, the compound will be retained in the brain due to its size and charge. The cleavage of the drug from the oxidized carrier will also occur in both the brain and the periphery, and if this cleavage occurs at a more rapid rate than the efflux of complex from the brain, a sustained release of the drug in the brain will be achieved. In the case of melanin or tyrosinase, a drug-carrier complex is prepared by coupling the melanin or tyrosinase to nicotinyl chloride as described by Bodor, N. et al., supra.

A further alternative method for delivering melanin or tyrosinase to target areas of the brain is to transport the tyrosinase gene into the brain by means of a defective Herpes simplex virus-1 (HSV-1) vector using a method described by Geller, A.I. et al., *Science* 241, 1667 (1988). Particularly, the defective HSV-1 vector described by Geller, A.I. et al., supra. is pHSVlac, which contains the *Escherichia coli lacZ* gene under the control of the HSV-1 immediate early 4/5 promoter.

In order to use this HSV-1 vector in the present invention, the tyrosinase gene (as isolated and identified by Huber, M. et al., *Biochemistry* 24, 6038 (1985)) is inserted into the defective HSV-1 vector in place of the *E. coli lacZ* gene using conventional techniques. This new vector containing the tyrosinase gene can then enter the brain where the tyrosinase gene will be replicated and transcribed to produce tyrosinase which in turn will catalyze melanin production in the immediate vicinity of the target cells.

The tyrosinase gene may also be introduced into the mammalian system using DNA constructs for retrovirus packaging cell lines as described in U.S. Pat. No. 4,861,719, the disclosure of which is incorporated herein by reference. In this procedure, a cell line containing a DNA construct such as pPAM3 (ATCC No. 40234) is used to transmit high titers of retroviral vectors which carry tyrosinase gene. An example of a useful cell line for this purpose is PA317 (ATCC No. CLR 9078).

Useful DNA constructs such as pPAM3 are constructed by deleting all of the cis-acting elements except for the tRNA binding site from the genome of a replication-competent retrovirus. The particular cis-acting elements which are deleted are: the packaging signal; the site for initiation of second strand DNA synthesis; the site required for translation of reverse transcriptase during first strand DNA synthesis; and the provirus integration signal.

The retrovirus vectors produced by PA317 cells are capable of infecting a variety of hosts including mouse, rat, cat, dog and human cells. Hemopoietic progenitor cells from human bone marrow and mouse embryo cells have been infected by retroviral vectors secreted from PA317 cells. The vector titer from the PA317 cells is very high (up to $10^7$ colony forming units/ml), and therefore, these cells are useful in mammalian gene therapy.

As with most neurologic drugs, there is no established dosage of melanin or tyrosinase. The regimen is determined empirically for each patient. The optimal dose is that which produces maximal improvement with tolerated side effects. For example, an initial dose of 0.5–1.0 gm/day with the total daily dosage increasing in increments not more than 0.75 gm every three to seven days as tolerated, is a recommended regimen. Although the optimal therapeutic dosage should not exceed 8 gm per day, patients may be given more as required. It is worth emphasizing that in both of the above cases, optimal dosage is determined empirically and balances the benefits and adverse side effects.

F. Examples

The invention is further illustrated by the following non-limiting examples. Example 1 demonstrates melanin's capability of chelating toxins such as MPTP. Example 2 shows that toxin-induced Parkinson's disease can be prevented if the toxin cannot bind to melanin in the brain. Since administered melanin can chelate toxins, it prevents the toxins from binding to melanin in the brain and causing neurodegenerative diseases. Example 7 demonstrates that melanin can be used to aid neuron recovery. Example 8 shows the use of melanin for the treatment of Parkinson's disease.

EXAMPLES 1–4

Extractions of Melanin

Melanin produced in the following examples was extracted from the growth medium by the following procedure.

Cultures were filtered through glasswool to remove mycelium. Alternatively, particulate matter and cells were removed from the growth medium by centrifugation at 5,000×gravity. The pH of the melanin containing medium was then reduced to about 3.0 with HCl. The precipitated melanin was removed by centrifugation at 6,800×gravity. The precipitate was then removed and resolubilized at pH 8.0. The resolubilized melanin was washed by doubling the value of the liquid with sterile distilled H₂O. The process of precipitation, removal, resolubilization and washing is repeated 4 times in order to substantially remove any non-precipitable impurities. The product may be dried to completion in an oven at 200° C. for 48 hours, if desired.

EXAMPLE 1

Conventional Melanin Production

This Example sets forth a conventional method for the production of melanin as taught by Hopwood, D.A. et al., "Genetic Manipulation of Streptomyces: A Laboratory Manual" The John Innes Foundation (1985).

Melanin production by *Streptomyces lividans* TK64 (pIJ702).

Preparation of Growth Medium

MMT MEDIUM was prepared from the following ingredients as described below.

MM MEDIUM:

| | |
|---|---|
| L-asparagine | 0.5 g |
| K₂HPO₄ | 0.5 g |
| MgSO₄.7H₂O | 0.2 g |
| FeSO₄.7H₂O | 0.01 g |
| H₂O | 1000 ml |

The ingredients were dissolved in water, adjusted to pH 7.0–8.2 with NaOH, 100 ml placed into 500 ml flasks, and autoclaved for 20 minutes.

The following sterile stocks were prepared:

| | | |
|---|---|---|
| *Difco Casaminoacids | (30%) | (50x Stock) |
| *Glucose | (50%) | (50x Stock) |
| *CuSO₄.5 H₂O | (0.50%) | (1000x Stock) |
| *Tyrosinase Inducer: | | |
| L-methionine | (1%) | |
| L-tyrosine | (3%) | (33.3x Stock) |
| L-leucine | (5%) | |
| *Tiger Milk: | | |
| L-arginine | (0.75%) | |
| L-cystine | (0.75%) | |
| L-histidine | (1.0%) | (133.3x Stock) |
| DL-homoserine | (0.75%) | |
| L-phenylalanine | (0.75%) | Does not dissolve |
| L-proline | (0.75%) | completely forms a |
| adenine | (0.15%) | white, milk-like |
| uracil | (0.15%) | solution |
| nicotinamide | (0.01%) | |
| thiamine | (0.01%) | |

*All of these stocks were autoclaved prior to making the medium.

The following ingredients were combined to prepare MMT medium:

| | |
|---|---|
| 100 ml | MM MEDIUM |
| 2 ml | Casaminoacids |
| 2 ml | Glucose |
| 750 ul | Tiger Milk |

For tyrosine and melanin production, the following ingredients were also included:

| | |
|---|---|
| 100 ul | CuSO₄.5 H₂O |
| 3 ml | Tyrosinase Inducer |

Inoculation and Growth of TK64 (pIJ702)

A small amount of the bacteria were scraped from the top of the plate and transferred into 10 ml of sterile water which was mixed and pipetted into six-500 ml flasks containing 100 ml of MMT. Cultures were grown at 30° C., and 120 RPM for 3 days.

Results

Melanin was purified as described above. The yield of melanin was about 100 mg/l, dry weight.

EXAMPLE 2

Production of Melanin In A Bioreactor

Preparation of Growth Medium

The growth medium was prepared as in Example 4. The medium contains 1.5 grams per liter of tyrosine. This medium contains no glucose or other carbon source except amino acids.

Inoculation and Growth of TK64 (pIJ702)

Spore stock of *S. lividans* TK64 (pIJ702) was diluted 1:10 in water. A starter culture was produced by adding 50 μl of dilute spore stock to 250 ml of culture medium in a 1 liter flask. The starter culture was incubated at 30° C. with shaking until it reached mid-log phase.

Starter culture was then transferred to a 30 liter fermentor containing 20 liters of growth medium. Incubation was at 30° C. with constant mixing at 225 RPM until the optical density reached a constant. Aeration during fermentation was by constant air flow at 1 liter of air per minute for 40 hours, and by 2.5 liters per minute for 40–60 hours, then by 3.0 liters per minute for the remaining 60–120 hours.

Results

Melanin was purified as described above. The yield of melanin was about 1.7 grams per liter dry weight.

EXAMPLE 3

Production of Melanin In A Bioreactor

Preparation of Growth Medium

The growth medium was prepared as in Example 4. The medium contains 1.5 grams per liter of tyrosine. This medium contains no glucose or other carbon source except amino acids.

Inoculation and Growth of TK64 (pIJ702)

Spore stock of *S. lividans* TK64 (pIJ702) was diluted 1:10 in water. A starter culture was produced by adding 50 μl of dilute spore stock to 250 ml of culture medium in a 1 liter flask. The starter culture was incubated at 30° C. with shaking until it reached mid-log phase. Starter culture was then transferred to a 42 liter fermentor containing 35 liters of growth medium. Incubation was at 30° C. with constant mixing at 225 RPM until the optical density reached a constant. Aeration was by constant airflow at 1.5 liters of air per minute for 36 hours, 4.0 liters per minutes for 36–48 hours, and 5.0 liters per minute for the final 48–120 hours. Antifoam was added daily after 48 hours.

Results

Melanin was purified as described above. The yield of melanin was about 2.0 grams per liter.

EXAMPLE 4

Production of Melanin Analogs

A. Preparation of the Growth Medium

MMT MEDIUM was prepared from the following ingredients as described below.

MM MEDIUM:

| | |
|---|---|
| L-asparagine | 0.5 g |
| K₂HPO₄ | 0.5 g |
| MgSO₄.7H₂O | 0.005 g |

-continued

MM MEDIUM:

| FeSO$_4$.7H$_2$O | 0.01 g |
|---|---|
| H$_2$O | 1000 ml |

These ingredients were dissolved in water, adjusted to pH 7.0–7.2 with NaOH, 100 ml placed into 500 ml flasks, and autoclaved for 20 minutes.

| *Casein-Peptone Hydrolyzate | (30%) | (50x Stock) |
|---|---|---|
| *Glucose | (50%) | (50x Stock) |
| *CuSO$_4$.5 H$_2$O | (0.50%) | (1000x Stock) |
| *Tyrosinase Inducer: | | |
| L-methionine | (1%) | |
| L-tyrosine | (3%) | (33.3x Stock) |
| L-leucine | (5%) | |
| *Tiger Milk: | | |
| L-arginine | (0.75%) | |
| L-cystine | (0.75%) | |
| L-histidine | (1.0%) | (133.3x Stock) |
| DL-homoserine | (0.75%) | |
| L-phenylalanine | (0.75%) | Does not |
| L-proline | (0.75%) | dissolve |
| adenine | (0.15%) | completely forms |
| uracil | (0.15%) | a white, milk- |
| nicotinamide | (0.01%) | like solution |
| thiamine | (0.01%) | |

*All of these stocks were autoclaved prior to making the medium.

The following ingredients were combined to prepare MMT medium:

| 100 ml | MM MEDIUM |
|---|---|
| 2 ml | Casein-Peptone Hydrolyzate |
| 2 ml | Glucose |
| 750 ul | Tiger Milk |
| 100 ul | CuSO$_4$.5 H$_2$O |
| 3 ml | Tyrosinase Inducer |

B. Inoculation and Growth of the *Streptomyces lividens* plasmid pIJ702

The *Streptomyces lividens* containing plasmid pIJ702 was inoculated into the MMT growth medium at a rate of $2 \times 10^5$ spores/ml. The *Streptomyces lividens* was then allowed to grow for 24 hours at 30° C. and pH 6.8 with 85% dissolved oxygen provided to the media.

C. Additions to the Growth Medium

After the *Streptomyces lividens* had been growing for 24 hours, tyrosine and metal ions were added to the growth medium. The tyrosine was added to a final concentration of 1.6 grams/liter, CuSO$_4$.5H$_2$O was added to a final concentration of 0.2 grams/liter and FeCl$_3$ was added to a final concentration of 4 mM.

D. Purification of A Melanin Analog

After 72 hours of fermentation following the addition of the tyrosine and metal ions, the melanin analog was extracted from the growth medium by the following procedure.

Cultures were filtered through glasswool to remove mycelium. Alternatively, particulate matter and cells were removed from the growth medium by centrifugation at 5,000×gravity. The pH of the melanin containing medium was then reduced to about 3.0 with HCl. The precipitated melanin was removed by centrifugation at 6,800× gravity. The precipitate was then removed and resolubilized at pH 8.0. The resolubilized melanin was washed by doubling the amount of the liquid with sterile distilled H$_2$O. The process of precipitation, removal, resolubilization and washing was repeated 4 times in order to substantially remove any non-precipitable impurities. The product may be dried to completion in an oven at 200° C. for 48 hours, if desired.

EXAMPLE 5

Affinity of Melanin for MPTP

1-Methyl-4-phenyl-1,2,5,6-tetrahydropyridine (MPTP) is synthesized in accordance with the method described by Schmidle and Mansfield (1955). Purity and identity are confirmed by thin-layer chromatography and gas chromatography-mass spectrometry.

Melanin from beef eyes is prepared according to Potts, A.M., *Ophthalmol.* 3, 405 (1964). The pigment is finally suspended in distilled water to a concentration of 10 mg (by dry weight) per ml suspension. It has been found that the melanin content of pigment granules from beef eyes is approximately 50% (Larsson et al., supra), which gives a concentration of 5 mg of pure melanin per ml suspension.

Synthetic dopamine melanin is prepared by autooxidation (Lyden et al., supra). The dopamine melanin suspension (in distilled water) is adjusted to contain 5 mg melanin per ml. Both pigment suspensions are stored at 2° C.

The binding of MPTP to the melanins is analyzed as previously described in detail by Lyden et al., supra. Six and one-half ml of various concentrations of MPTP (5.7 $\mu$M–1.2 mM) are mixed with 0.5 ml aliquot portions of melanin suspension. The reaction mixtures are incubated at room temperature for one hour. Reference samples contain distilled water instead of melanin. The mixtures are then centrifuged at 35,000×g for 10 minutes and the concentration of free MPTP in supernatants is measured spectrophotometrically at 243 nm after appropriate dilution. The uptake of MPTP on melanin is calculated from the differences in concentrations between the supernatants and the reference samples.

From the obtained data, the classes of binding sites, association constants and the binding capacity of the melanins are estimated according to Scatchard, G. et al., *J. Am. Chem. Soc.* 79, 12 (1957). As the molecular weight of melanin is unknown, the value for the number of binding sites is expressed as mol per mg melanin. The calculations are based on a melanin content of 2.5 mg per incubation.

MPTP is bound to both isolated beef eye melanin and synthetic dopamine melanin in vitro.

The calculated binding parameters are shown in Table 2. The association constants (K) are expressed as $M^{-1}$, and the number of binding sites (n), as $\mu$ mole per mg melanin.

TABLE 2

Binding Parameters for the Interaction of MPTP with Melanin

| Beef-eye melanin | $n_1 = 0.09$ | $K_1 = 2.32 \times 10^5$ |
|---|---|---|
| | $n_2 = 0.44$ | $K_2 = 1.22 \times 10^3$ |
| Dopamine melanin | $n_1 = 0.08$ | $K_1 = 5.82 \times 10^5$ |
| | $n_2 = 0.05$ | $K_2 = 1.22 \times 10^4$ |
| | $n_3 = 0.14$ | $K_3 = 7.68 \times 10^2$ |

Curvilinear Scatchard plots are observed for both melanins, which indicates that more than one binding class must be implicated. The data for the binding of MPTP to beef eye melanin could be fitted by the assumption of two classes of binding sites and to dopamine melanin by three classes of binding sites. Both beef eye and dopamine melanin contained a small number of binding sites ($n_1$) with a high association constant ($K_1$) and a great number of binding sites ($n_2$ and $n_3$, respectively). The concordance between the association constants indicates a binding to identical sites on the two melanins. In addition, a small intermediary binding to dopamine melanin was found ($n_2$) which reflects certain differences in chemical structure between the two melanins—beef eye melanin is obtained from tyrosine as precursor.

The total binding capacity ($\Sigma n$) of beef eye melanin is 0.53 $\mu$mol/mg melanin. This is probably due to the higher content of carboxyl groups in beef eye melanin (Nicolaus, R.A., in *Melanins*, E. Lederer, Ed., Hermann, Paris (1968)). It is interesting to note that the total binding capacity of MPTP to beef eye melanin is of the same magnitude as that of chlorpromazine and cloroquine (Larsson et al., supra), two drugs that are known to give melanin related side effects.

Thus, it can be seen that melanin is an effective chelator of MPTP, a neurodegenerative disease-causing substance.

EXAMPLE 6

Protection from MPTP Induced Parkinson's Disease

The ability to protect a mammal from toxin-induced neurodegenerative disease, such as Parkinson's disease, is examined by treating monkeys with MPTP in a state in which MPTP could not bind to melanin.

Thirteen male monkeys (*Macaca fascicularis*) 5 to 8 years old, weighing 3.5 to 4.8 kg, are studied. Four animals are naive controls. Nine receive daily (0.35 mg per kg) injections of MPTP i v. for four days. Three animals (M1-3) who received no chloroquine are the untreated controls. Six animals are pretreated with chloroquine (4 mg per kg) intramuscularly; three (S1-3) are pretreated for 12 days, and three (L1-3) for 24 days. All six pretreated animals continue to receive chloroquine injections during MPTP administration and for 10 days following MPTP exposure. The neurological examination evaluates the spontaneous movement, tremor, tone and deep tendon reflexes. A zero score in each category reflects a total loss of spontaneous movement, maximum tremor, maximum increase in tone, or maximum hyperreflexia. Deep tendon reflexes examined are brachial radials, knee jerk, and ankle jerk. Muscle tone tests evaluate protraction-retraction, abduction-adduction and flexion-extension in both upper and lower extremities. Tremor is rated on severity and the number of extremities involved. Spontaneous movement is evaluated in the morning over a 30 minute period. The rating scale consists of arbitrary units which are weighted to reflect the disturbances most prominent in MPTP-treated monkeys. Control values are the maximum (normal) score for each element of the exam and all control animals fell within 10% of the control values. The sum of scores for the four elements is multiplied by 5.26 to provide a total score with a value of 100 for control animals. The results are shown in Table 3.

TABLE 3

Neurological Effects of Chloroquine on MPTP Neurotoxicity in Monkeys

| | Spontaneous Movement | Neurological Status | | | Total |
|---|---|---|---|---|---|
| | | Tremor | Tone | Reflexes | ($\times$ 5.26) |
| Control | 10 | 5 | 2 | 2 | 100 |
| MPTP | 1 | 1 | 0.5 | 0.5 | 16 |
| M1 | 1 | 1 | 2 | 1.5 | 29 |
| M2 | 1 | 0 | 0.5 | 0 | 8 |
| Short-Term Chloroquine/ MPTP and MPTP | | | | | |
| S1 | 3 | 4 | 2 | 2 | 58 |
| S2 | 3 | 3 | 1 | 1 | 42 |
| S3 | 3 | 3 | 2 | 1 | 47 |
| Long-Term Chloroquine/ MPTP and MPTP | | | | | |
| L1* | 0 | 2 | 1.5 | 1 | 24 |
| L2 | 5 | 5 | 1 | 1 | 63 |
| L3 | 7 | 5 | 2 | 2 | 84 |

*Chloroquine level is 36% of that in other monkeys monitored.

The behavior of the monkeys receiving MPTP alone is similar to that of monkeys previously exposed to MPTP as described in other reports (Schwartzman, R. et al., *Brain Res.* 358, 137 (1985)). On the fifth day after MPTP exposure the animals manifest decreased mobility and spontaneous movement, abnormal posture, rigidity of the neck and limbs, increased muscle tone, hyperactive reflexes, tremor of upper extremities, and lack of vocalization (Table 3).

Five of the six monkeys pretreated with chloroquine are partially protected from MPTP-induced parkinsonian clinical symptoms. Of the three monkeys receiving long-term treatment with chloroquine, one animal (L-3) is almost completely protected except for a slight decrease in spontaneous movement. A second animal in this group (L-2) is also protected from the severe effects of MPTP. Although it exhibits modest rigidity, the monkey manifests no tremor, moves about the cage freely and vocalizes extensively. However, one animal (L-1) demonstrates motor deficits as severe as monkeys receiving MPTP alone; the reasons for the failure of chloroquine protection are described below. All three animals receiving short-term chloroquine pretreatment are partially protected from MPTP neurotoxicity; although they have some rigidity, all move about the cage readily, eat well, vocalize extensively and show only modest tremor.

To determine dopamine and homovanillic acid (HVA) levels, brain samples (10-20 mg wet weight) are homogenized in 300 $\mu$l of 0.4 M perchloric acid and centrifuged at 4° C. for 10 minutes at 1,000 g. Aliquots of the supernatants are analyzed directly by reverse-phase high performance liquid chromatography (HPLC) on an ODS-3 column (Whatman Chemical Separation) with a Pellosil $C_8$ guard column (Alltech Associates). The mobile phase for this system is acetate-phosphate/methanol (95:5) which includes EDTA and sodium heptanesulphonate as an ion-pairing agent (Bioanalytical Systems, Inc.). Detection is done electrochemically on a glassy carbon electrode (Bioanalytical Systems Inc.) at an applied voltage of 0.65 V. Plasma levels of chloroquine are determined by HPLC with UV detection. Samples are deproteinated with 0.2 vol. of 25% trichloroacetic acid followed by centrifugation at 4° C. for 30 minutes at 1,000 g. Supernatants are removed, lyophilized overnight and reconstituted with 80 μl of 0.1 M perchloric acid. Samples are analyzed directly using reverse-phase HPLC with a Whatman ODS-3 column (Whatman) and Pellosil C$_8$ guard column (Alltech). The mobile phase for this system is 40% acetonitrile, 0.1 M sodium phosphate (pH 3.0) with 75 mM perchloric acid. Absorption is detected at 343 nm (Bergqvist, Y. et al., *Chromat.* 221, 2503 (1985)). Tyrosine hydroxylase (TH) activity is assayed by the tritium release method of Nagatsu, T. et al., *Analyt. Biochem.* 9, 122 (1964) and Levine, R. et al., *Analyt. Biochem.* 143, 205 (1984), employing modified reaction conditions of Coyle, J. *Biochem. Pharmac.* 21, 1935 (1972). Supernatant fluid (50 μl) from brain homogenate (1 g tissue in 20 vol 50 mM Tris, H 7.4) are added to 7 ml glass scintillation vials containing 5 μl 6 DL-6-methyl-5,6,7,8-tetrahydropterine (2.8 mg ml$^{-1}$), 5 μl FeSO$_4$ (2.78 mg ml$^{-1}$) and 1 μC of ring labelled [$^3$H]tyrosine. Mixtures are incubated 30 minutes at 37° C. and the reaction terminated by adding 50 μl 3 M Na$_2$CO$_3$, pH II.6. Toluene/isoamyl alcohol scintillant (5 ml) is then added directly to the vial and the contents mixed for 10 seconds. The results are shown in Table 4. The aqueous and organic phases are allowed to separate and the $^3$H$_2$O extracted into the organic phase determined.

ity, show much slighter reductions in levels of dopamine and TH, as well as TH-immunoreactive fibres and terminals, than MPTP-treated animals.

Neuropathological findings fit well with the clinical and neurochemical observations. Representative neuromelanin-stained sections through the substantia nigra from each animal are rank-ordered for cell loss by two naive observers whose rankings are identical and closely parallel the neurochemical and clinical results. The correlation coefficient of the ranking with the caudate dopamine values (R) is 0.90. The greatest reduction in nigral cell number occurs in animals given MPTP alone (data not shown). Chloroquine-pretreated animals have more surviving neuromelanin-containing neurons, with the greatest number of cells remaining in the long-term pretreatment group.

Thus, short-term treatment with chloroquine provides partial protection against clinical, neurochemical and neuropathologic effects of MPTP, and in two of three animals, long-term treatment provides more pronounced protection. Why one of the monkeys receiving long-term chloroquine treatment (L-1) is not protected against the effects of MPTP is not known. Chloroquine in plasma is assayed in four of the monkeys immediately before administration of MPTP. Monkeys S-3, L-2 and

TABLE 4

| | Biochemical Effects of Chloroquine on MPTP Neurotoxicity in Monkeys | | | | | | | |
|---|---|---|---|---|---|---|---|---|
| | Chloroquine in plasma (ng ml$^-$) | PUTAMEN | | | | CAUDATE | | |
| | | DA | HVA | HVA/DA | TH (% control) | DA | HVA | HVA/DA | TH (% control) |
| | | (nmol per g tissue) | | | | (nmol per g tissue) | | |

| | Chloroquine in plasma (ng ml$^-$) | DA | HVA | HVA/DA | TH (% control) | DA | HVA | HVA/DA | TH (% control) |
|---|---|---|---|---|---|---|---|---|---|
| Control | | | | | | | | | |
| C1 | | 47.0 | 43.5 | 0.9 | | 62.4 | 43.8 | 0.7 | |
| C2 | | 42.1 | 12.1 | 0.3 | | 39.1 | 17.4 | 0.4 | |
| C3 | | 73.4 | 34.6 | 0.5 | | 79.1 | 17.3 | 0.2 | |
| C4 | | 64.1 | 36.2 | 0.6 | | 53.5 | 29.9 | 0.6 | |
| MPTP | | | | | | | | | |
| M1 | | 1.2 | 5.6 | 4.7 | 11.8 | 0.6 | 4.1 | 7.5 | 6.9 |
| M2 | | 1.4 | 2.6 | 1.8 | 10.8 | 0.6 | 1.7 | 2.8 | 8.4 |
| M3 | | 1.8 | 5.8 | 3.2 | 21.0 | 0.9 | 8.7 | 9.4 | 17.9 |
| Short-term Chloroquine and MPTP | | | | | | | | | |
| S1 | ND* | 5.2 | 10.1 | 1.9 | 20.0 | 1.1 | 8.0 | 7.5 | 14.0 |
| S2 | ND | 5.0 | 8.6 | 1.7 | 23.3 | 1.3 | 10.5 | 8.1 | 18.7 |
| S3 | 300 | 11.2 | 9.8 | 0.9 | 29.8 | 7.6 | 9.2 | 1.2 | 22.6 |
| Long-term Chloroquine and MPTP | | | | | | | | | |
| L1 | 120 | 1.1 | 5.2 | 4.7 | 7.2 | 0.5 | 5.7 | 11.1 | 8.1 |
| L2 | 310 | 16.0 | 20.1 | 1.3 | 58.5 | 11.0 | 15.7 | 1.4 | 39.5 |
| L3 | 370 | 29.6 | 18.3 | 0.6 | 101.0 | 17.3 | 5.9 | 0.3 | 77.1 |

*Not determined.

Results of neurochemical analyses closely parallel the clinical findings (Table 4). In monkeys receiving MPTP alone, amounts of dopamine, homovanillic acid (HVA) and tyrosine hydroxylase activity (TH) are markedly reduced in both the caudate and putamen. Dopamine is depleted to about 1% of control, whereas HVA was at about 10% of control. The resulting increased HVA/-dopamine ratio in the MPTP animals presumably reflects the greater turnover of dopamine in residual dopamine neurons. In monkeys receiving MPTP alone, TH immunocytochemical preparations (Kitt, C.A. et al., *Neuroscience* 17, 1089 (1986)) reveals a pronounced reduction in the density of TH immunoreactive fibres and terminals in the putamen and to a lesser extent in the caudate nucleus as compared to controls (data not shown). The five chloroquine pretreated monkeys, which are clinically protected from MPTP neurotoxicity, L-3, which are protected against the effects of MPTP, have 300, 310 and 370 ng ml$^{-1}$ chloroquine respectively (≈1 μM of which half is bound to plasma protein). In contrast, monkey L-1, which developed a parkinsonian syndrome, has a plasma level of 120 ng ml$^{-1}$. Presumably, the failure of drug protection results from the diminished availability of chloroquine in this monkey.

The partial protection of monkeys from MPTP neurotoxicity elicited by chloroquine, together with the high-affinity interactions of MPP+ with neuromelanin (D'Amato, R.J. et al., *Science* 231, 987 (1986); D'Amato, R.J. et al., *Neurochem.* 48, 653 (1987)) indicates that destruction of dopamine neurons in the substantia nigra by exposure to low doses of MPTP is dependent upon interactions of MPP+ with neuromelanin. By inhibiting the binding of MPP+ to neuromelanin, chloroquine may reduce intraneuronal sequestration of MPP+, resulting in reduced toxicity to organelles such as mitochondria (Nickles, W.J. et al., *Life Sci.* 36, 2503 (1985)).

Example 1 demonstrates that melanin is capable of binding MPTP, a toxin which causes a neurodegenerative disease. Example 2 shows that the disease is caused by the binding of MPTP to melanin in the brain. Since melanin is capable of binding MPTP, it is evident that melanin which is administered to a mammal will bind an environmental neurotoxin such as MPTP, thus preventing a neurodegenerative disease such as Parkinson's disease.

EXAMPLE 7

Melanin Administration to Aid Neuron Recovery

Male C57BL/6J IMR mice 6–8 weeks of age are used throughout except in one experiment (see below) in which CB6F$_1$ [(BALB/cByJ IMR×C57BL/gJ IMR)F$_1$] mice of a similar age are used. Mice are housed five per cage in plexiglass cages with free access to food and water in a colony room maintained at 23°±1° C. Fluorescent lighting in the room is automatically turned on at 06.00 hours and off at 18.00 hours.

[$^3$H]DA (31.6 Ci/mmol) and [$^3$H]mazindol (19.6 Ci/mmol) are purchased from New England Nuclear (Boston, Mass.). MPTP is purchased from the Aldrich Chemical Company (Milwaukee, Wis.) and converted to the hydrochloride salt as described in Irwin, I. et al., *Neurology* 35, 619 (1985). Pargyline hydrochloride is a gift from Abbott Laboratories (Chicago, Ill.). Silver nitrate is purchased from Fisher Scientific Co. (Fairlawn, N.J.). All other compounds are purchased from Sigma Chemical Co. (St. Louis, Miss.).

C57 black mice are administered MPTP hydrochloride intraperitoneally according to either one of two schedules: (1) 30 mg/kg/day for 10 days, or (2) 20 mg/kg/hour for 4 hours. The one group of CB6F$_1$ mice used in this study is administered MPTP according to the following schedule: 50 mg/kg/day for 13 days. This group is used only for anatomical studies looking for cell loss in the substantive nigra cells (SNc). All other studies are performed in C57 black mice.

MPTP hydrochloride is dissolved in distilled water at a concentration such that it could be injected at a desired dosage on a 1 ml/100 g body weight basis. Dose is expressed as the free base.

Melanin is isolated from *Streptococcus antibioticus*. Melanin is administered to the test mice at a dose of 10 mg/kg/day following the MPTP treatment by injection into the cerebrospinal fluid until the mice are killed.

The mouse striatum is obtained by placing the brain on its dorsal surface and making two coronal cuts; the first at the caudal end of the olfactory bulbs, the second at the level of the optic chiasma. After placing the resulting brain slice on its rostral surface, one horizontal cut is made just below the corpus callosum and another just above the anterior commissure. Remaining parietotemporal cortex is trimmed away using the external capsule as a landmark. Septal tissue lying between the caudate nuclei is removed by cutting along the tissue planes created by the frontal horns of the lateral ventricles. Striatal tissue thus isolated weighs approximately 20 mg per animal. Immediately after dissection, tissue is wrapped in aluminum foil and stored in liquid nitrogen until assay, with the exception of tissue for uptake studies which is used immediately.

The striatum is weighed, placed in a tube containing 1 ml of 0.4 normal perchloric acid, then homogenized with a Beckman polytron at a setting of 5 for 10 seconds. The homogenate is centrifuged at approximately 20,000×g for 15 minutes. Concentrations of dopamine (DA), DOPAC and HVA in the supernatant are determined by reverse-phase liquid chromatography coupled with electrochemical detection according to the method of Mayer, G.S. et al., *J. Chromatogr.* 255, 533 (1983), with minor modifications. The mobile phase is prepared by mixing 965 ml of 0.15 M monochloroacetic acid with 35 ml of acetonitrile and adding 193 mg of sodium octyl sulfate. This solution is filtered and degassed and then 18 ml of tetrahydrofuran are added. Using this mobile phase at a flow rate of 1.3 ml/min, DA, DOPAC and HVA are resolved using a 4.6 mm×25 cm C-18, 5 $\mu$ column (Brownless Labs). Detection and quantitation are performed using a dual series electrode detector (Coulochem Model 5100, Environmental Systems Associates, Wiggins, Mass.). Electrode potentials are set at +0.4 V (electrode 1) and −0.3 V (electrode 2). The response on electrode 2 is monitored (10 mV strip chart recorder) and used for quantitation relative to peak heights of known amounts of standards.

The in vitro accumulation of [$^3$H]DA by crude striatal synaptosomal suspensions is measured using the method of Snyder, S.H. et al., *J.Pharmacol.Exp.Ther.* 165, 78 (1968) with minor modifications. Briefly, crude synaptosomal suspensions are prepared by homogenizing striatal tissue in 50 vols. (w/v) of ice-cold 0.32 M sucrose, then centrifuging the homogenate for 10 minutes at 1,000×g. Aliquots (0.1 ml) of the supernatant are added over ice to tubes containing 1.9 ml of Krebs-Ringer phosphate buffer which contained these in final concentrations: 118 mM NaCl, 16.2 mM Na$_2$HPO$_4$, 4.7 mM KCl, 1.3 mM CaCl$_2$, 1.2 mM MgSO$_4$, 1.1 mM ascorbic acid, 11.1 mM glucose. 1.3 mM EDTA, <0.125 mM pargyline along with equimolar mixtures of [$^3$H]DA and native DA at concentrations ranging from 0.025 to 0.5 $\mu$M. After vortexing, tubes (except temperature blanks) are incubated in a waterbath at 37° C. for five minutes, then returned to ice. Synaptosomes are harvested by filtration. Filters are rinsed twice with 5 ml aliquots of physiological saline. Radioactivity in the filters is quantified by liquid scintillation spectroscopy. Assays are performed in sextuplicate at each DA concentration, with half of the samples serving as blanks. Active uptake is defined as the difference between [$^3$H]DA (PM/mg tissue/5 min.) incubation at 37° C. after correction for uptake at 0°–4° C.

The binding of [$^3$H]mazindol to striatal membranes is measured according to the method of Javitch, J.A. et al., *Eur.J.Pharmacol.* 90, 461 (1983).

Nerve terminal degeneration studies are performed using the method of Fink, R.P. et al., *Brain Research* 4, 369 (1967) (Procedure 1). This method makes possible selective silver impregnation of degenerating nerve fibers and terminals. Mice for these studies are killed under sodium pentobarbital anesthesia (40 mg/kg) by transcardial perfusion with 10% formal saline. The brain is immediately removed and stored in perfusion fluid at 0°–4° C. for at least one week before being sectioned on a freezing microtome. 30 $\mu$m coronal sections are collected in 5% formal saline, then stained with silver according to Fink et al., supra. Mice for these studies are killed one and three days after treatment with either 20 mg/kg/h×4 or 30 mg/kg/day×10 of MPTP (n=3 for each group) or 10 or 20 days after treatment with melanin.

Cell bodies in the SNc are examined in both frozen and paraffin embedded sections after fixation in 10% formal saline. Frozen sections (30 μm) are stained with silver according to Fink et al., supra. Mice for those studies are treated with either 20 mg/kg/h×4 or 30 mg/kg/day×10 of MPTP and killed one or three days after the last MPTP injection, at various intervals after treatment with melanin is initiated. Alternating serial paraffin sections (8 μm) through the entire SNc are stained with either hemotoxylineosin or luxol fast blue-cresyl violet. C57 black mice used in these studies are treated with 30 mg/kg/day×10 of MPTP and killed 10 days after the last drug injection. CB6F$_1$ mice used in these studies are treated with 50 mg/kg/day×13 and killed 21 days after the last drug injection.

The results which are obtained following MPTP treatment and melanin treatment after halting the MPTP treatment are discussed below.

Mice administered 30 mg/kg/day×10 of MPTP and killed one week later show a 67% reduction in striatal DA content (Table 1). This result agrees well with that of Heikkila, R.E. et al., Nature 311, 467 (1984). Mice administered 20 mg/kg/h×4 of MPTP show a comparable depletion of striatal DA (Table 5). The long-lasting depletion of DA induced by this shorter MPTP regimen is dose-related. No lethality is produced by the 2.5, 5 and 10 mg/kg/h×4 MPTP regimens. Approximately 20% of the mice die after the 20 mg/kg/h×4 regimen. Larger MPTP does regimens kill more than 50% of the animals. One day after cessation of MPTP treatment, mice administered with the 20 mg/kg four-hour MTP regimen or the 30 mg/kg 10 day regimen could not be distinguished behaviorally from their control littermates by casual observation.

TABLE 5

Effect of 10-Day and 4-Hour MPTP Treatments on Mouse Striatal DA Content One Week Later

| Treatment | n | DA (μg/g) | % Depletion |
|---|---|---|---|
| Control | 10 | 10.7 ± 0.5 | — |
| MPTP 30 mg/kg/day × 10 | 5 | 3.5 ± 0.3* | 67 |
| MPTP 20 mg/kg/h × 4 | 5 | 2.8 ± 0.5* | 74 |

*Significantly different from control group (P < 0.05; two-tailed Student's t-test).

Along with reduced level of DA, mice treated with 20/mg/kg/h×4 of MPTP have decreased striatal concentrations of DOPAC and HVA. DOPAC is reduced from 0.96 (±0.14) μg/g to 0.28 (±0.02) μg/g and HVA from 1.38 (±0.05) μg/g to 0.60 (±0.06) μg/g (differences significant at 0.05 level). Mice administered 20 mg/kg/h×4 of MPTP and killed one week later also show decreased stiatal synaptosomal [$^3$H]DA uptake (Table 6). The $V_{max}$ was decreased by 62%. The $K_m$ was not changed.

TABLE 6

Kinetic Constants of [$^3$H]DA Uptake One Week after MPTP

| | $V_{max}$* | $K_m$(μm) |
|---|---|---|
| Control | 5540 ± 480 | 0.14 ± 0.02 |
| MPTP | 2080 ± 305** | 0.12 ± 0.02 |

*Expressed as cpm[$^3$H]DA/mg tissue/5 min.
**Significantly different from control.

The [$^3$H]mazindol binding site has recently been proposed as an additional dopaminergic terminal marker. Mice administered 20/mg/h×4 of MPTP and killed three weeks later also show a decreased number of [$^3$H]maxzindol binding sites (Table 7). The $B_{max}$ was reduced by 44%. The $K_4$ was unchanged.

TABLE 7

Kinetic Constants of [$^3$H]Mazindol Binding to Striatal Membranes Three Weeks After MPTP

| | $B_{max}$* | $K_4$(nm) |
|---|---|---|
| Control | 361 | 17.6 |
| MPTP 20 mg/kg/h × 4 | 201 | 17.3 |

*Expressed as pmol/g tissue.

Three of three mice administered 20 mg/kg/h×4 of MPTP and killed one day later for silver degeneration studies show a large amount of fine granular argyrophilic debris in their striata. Some fine granular degeneration is also found in the nucleus accumbens and olfactory tubercle, but in these regions it was much less dense. No such degeneration is found in identically treated sections of control mice, or in other brain regions visible in coronal brain sections at the level of the striatum. None of three mice treated with 20 mg/kg/h×4 of MPTP but pretreated with 25 mg/kg of pargyline, which blocks the dopaminergic neurochemical deficits induced by MPTP in mice (Heikkila, R.E. et TM 1 , supra) show any evidence of striatal terminal degeneration.

In frozen sections through the SNc stained with silver according to the Fink-Heimer method, two of the same three mice which show dense terminal degeneration in their striata show no sign of cell body destruction. The third animal has a few SNc cells which may have been undergoing degeneration. These few cell bodies stain intensely with silver, appear shrunken, and some have dendritic arbors which were argyrophilic and appear beaded. Cells with similar appearance have been interpreted as undergoing degeneration by various authors. Although formal counts of these neurons were not performed, affected neurons appear to represent only a very minor fraction of the total SNc cell population. In serial paraffin sections through the entire length of the SNc, there is no definite cell loss or glial reaction in C57 black mice treated with 30 mg/kg/day×10 (n=four experimental, two controls) or in CB6F1 mice treated with 50 mg/kg/day×13 (n=four experimental and four controls) of MPTP. Coded sections from control and experimental animals cannot be distinguished from each other by either of two observers. Mice from these two groups were killed 10 and 21 days, respectively, after drug treatment so as to optimize the possibility of detecting cell loss.

Determination of the level of striatal DA, its metabolites, and synaptosomal uptake at various times after 20 mg/kg/h×4 of MPTP reveals that substantial recovery in all of these parameters occurs with time. DA level rises from 28% of control one week after MPTP to 69% of control 15 months later. Three months after MPTP, there is still a 34% depletion of striated DA. Partial recovery of striatal DA also occurs after a 30 mg/kg/day×10 MPTP regimen. [$^3$H]DA uptake capacity likewise recovered with time. The $V_{max}$ of [$^3$H]DA striatal uptake increases from 37% of control one week after MPTP to 79% of control three months later (6238 (±520) CPM [$^3$H]DA/mg tissue/5 min in control mice vs. 4928 (±408) CPM [$^3$H]DA/mg tissue/5 min in MPTP mice). Over this same time period, DOPAC rises from 29% of control three months later (1.53±0.09 μg/g in controls vs. 1.03±0.03 μg/g in MPTP mice). HVA rises from 43% of control one week after MPTP (vida supra) to 80% of control three months later (1.36±0.11 μg/g in control vs. 1.09±0.04 μg/g in MPTP mice).

When melanin is given following MPTP treatment, the time period required for a similar recovery is reduced and recovery continues through the five-month examination. For example, the $V_{max}$ of [$^3$H]DA striatal uptake increases to 75% of control after 3.5 months of melanin treatment and increases to 85% after five months of melanin treatment.

These results clearly show that during the period tested, melanin is capable of aiding the recovery of neurons following an injury to the neurons. Since melanin is capable of aiding the recovery of neurons following an injury, melanin can be used to treat Alzheimer's disease.

Any of the melanins isolated in Examples 1-4 may also be administered in the same fashion to aid neuron recovery.

EXAMPLE 8

Melanin Treatment of Parkinson's Disease

Male squirrel monkeys (aged 2-3 years) are used for this study. MPTP (Delmar Chemicals) is converted to its hydrochloride salt, dissolved in sterile water to a final concentration of 1 mg/ml (as the free base) and filtered through a 0.22 μm millipore filter into sterile injectable vials. All injections are intraperitoneal.

Three different dosage schedules of MPTP are used. Monkey Group A receives four doses, 2 mg/kg each, which are given at two-hour intervals. Monkey Group B is treated over a five-day period. On day 1, a single 2 mg/kg dose is given. On day 3, two injections of 2 mg/kg each are given, six hours apart. On day 5, a 3 mg/kg dose is given followed by a 0.5 mg/kg dose four hours later (total dose: 9.5 mg/kg). Three doses of 3 mg/kg each are given to Monkey Group C, spaced at six-day intervals. Monkey Group D serves as a control.

After two or more doses of MPTP, increasing bradykinesia and frequent "nodding off" (characterized by closing of the eyes and a slow downward drift of the head) are observed in all animals. Fasciculations of the thigh muscles occur in Monkey Group A. A transient but striking behavioral syndrome is seen after each of the last three doses in Monkey Group A, and after the final two doses in Monkey Group B. This syndrome is characterized by repeated abrupt eye opening and shaking and extension of the extremities.

All monkeys eventually become profoundly akinetic, usually sitting hunched over in a tightly flexed posture. They exhibit a generalized increase in tone. Vocalization and oral intake were markedly diminished. Monkeys hold awkward postures for lengthy periods, and sometimes freeze in the middle of a movement. They are often unable to release their grip, getting stuck on the bars of the cage. Tremor and a flexed posture of the arms are seen in Monkey Group C.

Two days after receiving MPTP, one monkey in Group A is given one-fourth of a 2.5 mg bromocriptine tablet (Parlodel ®) and one-eighth of a 10/100 carbidopa/L-dopa combination tablet (Sinemet ®) orally. Within 30 to 60 minutes, the animal is fully mobile and appears almost normal for five hours. A similar response to the same treatment is observed on each of the next four days. Subsequently, the animal becomes less responsive to medication and is sacrificed on day 10. One monkey in Group B responds to Sinemet ® (one-eighth of a 10/100 tablet) with full mobility on day 9. However, on subsequent days, he becomes increasingly less responsive to medication, often appearing uncoordinated and shaky. This monkey is sacrificed on day 15. One monkey in Group C becomes nearly normal for 24 hours after a single dose of Sinemet ® (10/100) on day 25. Three days later, this monkey becomes profoundly hypokinetic, develops slow respirations, and dies.

After increased bradykinesis and frequent nodding-off are observed in the monkeys, several monkeys of Groups A, B and C are administered melanin by injection into the cerebrospinal fluid at a dose of 50 mg/kg daily. The melanin is isolated from *Streptococcus antibioticus*. Amelioration of the bradykinesia and rigidity are seen in the melanin-treated animals. The monkeys' overall functional ability and secondary motor manifestations also improved during the course of the melanin treatment.

Any of the melanins isolated in Examples 1-4 may be administered in the same fashion to treat Parkinson's disease.

EXAMPLE 9

Preparation of a Melanin/Boron Complex

Melanin analog from Example 4 is solubilized in water at pH 7. The solubilized melanin is then reacted with a 20-fold molar excess of the diazonium salt of 1-(4-aminophenyl)-1,2-dicarba-closo-dodecaborane having a natural abundance of Boron-10 isotope (20%). The resultant melanin/boron complex has about 10,000 boron atoms per molecule of melanin.

This procedure can also be used with the melanin of Examples 1-4 to yield similar melanin/boron complexes which are soluble in aqueous solution.

EXAMPLE 10

Preparation of Monoclonal $^{131}$I-Anti-CEA IgG

The preparation of monoclonal $^{131}$I-anti-CEA IgG is done in accordance with the procedure presented in Example 2 of U.S. Pat. No. 4,348,376. Particularly, female, 6-month-old, Balb/C mice are injected with 10-100 μg carcinoembryonic antigen (CEA) intraperitoneally, whereby the CEA is mixed in an equal volume (10-100 μl) of incomplete Freund's adjuvant. These injections are repeated one week later, and again two weeks later, but the last injection uses the intravenous route without adjuvant. Three to four days later, the mice are killed by cervical dislocation. The optimum time for obtaining antibody against a given antigen varies with the antigen, the route of administration, and the timing of immunization, as well as the interval between the last booster injection and the removal of the spleen cells.

The spleens are removed and placed in 60 mm Petri dishes containing either serum-free medium or Dulbecco's Modified Eagle's Medium (DMEM) with 20% fetal calf serum, at room temperature, and minced with scissors to disperse the cells. The cells are further liberated by agitation for 1-2 minutes on a Vortex mixer. The spleen cells are removed to a conical centrifuge tube and pelleted at 1,000 rpm, the supernatant is removed, the pellet tapped loose, and then resuspended in 5 ml of cold 0.17 NH$_4$Cl for 10 minutes to lyse red blood cells. Chilled DMEM with 20% fetal calf serum is added and the cells pelleted, and then again suspended in 10 ml DMEM supplemented with 20% fetal calf serum.

The myeloma cell lines used for fusion are maintained in stationary suspension cultures in DMEM with high glucose (4.5 g/L) and 20% fetal calf serum, in 5-10% $CO_2$ at a cell concentration between 100,000 and 1,000,000 per ml. The myeloma (plasmacytoma) cell lines can be P3/X63-Ag8, which is a Balb/C plasmacytoma derived from MOPC-21 (Svasti and Milstein, Biochem. J. 128, 427 (1972)), or a derivative thereof known as OF (Fazekas de St. Groth and Scheidegger, Basle Institute of Immunology, Basle, Switzerland), or 45.6TG1.7, which is a Balb/C line derived from MPC-11 (Margulies et al., Cell 8, 405 (1976)). All of these lines lack the enzyme hypoxanthine phosphoribosyl transferase (HPRT; E.C. 2.4.2.8) and are thus killed in a selective medium containing hypoxanthine, aminopterin, and thymidine (HAT), as described by Littlefield (Science 145, 709 (1964)).

The spleen cells obtained from the immunized animal are then fused with the plasmacytoma cells by using polyethylene glycol according to an adaptation of the method of Gelfer et al. (Somatic Cell Genetic. 3: 231-236, 1977). For example, a 30% polyethylene glycol solution is made by heating sterile polyethylene glycol 4000 (Merck, molecular weight of about 4,000) (0.5 g Polyethylene glycol +0.05 ml dimethyl sulfoxide (DMSO) +0.5 ml distilled water) and DMEM without serum to 41° C., and mixing 3 ml of polyethylene glycol with 7 ml DMEM without serum, pH 7.4-7.6, and kept at 37° C. until use. Fusions are made at room temperature. The myeloma cells ($10^6$-$10^7$) are washed twice in serum-free medium and then mixed with $1-3\times 10^7$ to $1-3\times 10^8$ spleen cells in 50 ml conical bottom centrifuge tubes (Falcon 2070). The cells are centrifuged at 250 xg for 5 minutes and the supernatant fluid is carefully aspirated. A 0.2 ml amount of the polyethylene glycol preparation is added, and the tube is gently agitated by hand to resuspend the cells. Next, the cells are centrifuged for 3 minutes at 250 xg and again at 400 xg for another 3 minutes, and then kept undisturbed for an additional 3 minutes. The cells are exposed to polyethylene glycol for about 8 minutes. Thereafter, about 5 ml of serum-free medium is added to the tube, the cells are resuspended gently, and then repelleted by centrifugation at 250 xg for 5 minutes. The supernatant is removed and the cells are suspended in 20 ml of serum-containing medium and incubated at 37° C., in a humidified incubator for 48 hour before being placed in microplates to which HAT medium is added. Alternatively, the cells are immediately suspended in 30 ml of a medium consisting of DMEM, 10% NCTC 109 medium (Microbiological Associates), 20% fetal calf serum (GIBCO), 0.2 units bovine insulin/ml (Sigma), 0.45 mM pyruvate, 1 mM oxaloacetate, and antibiotics of choice. Thymidine ($1.6\times 10^{-10}$ M) and hypoxanthine ($1\times 10^{-4}$ M) are added. The cells in this medium are distributed into 6 microplates (Linbro FB 96 TC) with 1 drop (about 50 μl) per well. The next day 1 drop of the above-specified medium containing thymidine and hypoxanthine, now with aminopterin ($8\times 10^{-7}$ M), is added to each well. Two drops of the medium of above is added 6-7 days later and clones appear microscopically between 10 and 20 days. The hypoxanthine-aminopterin-thymidine (HAT) medium can also be added immediately after the fusion, or at a later time. An improvement in the number of hybrids obtained is made when a feeder layer is added to each microwell. Here, human fetal fibroblasts are irradiated with 4500 r, and 1,000-2,000 such cells are added to each well, either the day before the fusion or directly to the fused cells and so dispensed with them into the microwells. After clones have appeared macroscopically, the medium is changed by removing most of the medium and adding fresh medium. After a second change of medium, the medium is left for at least 4 days and then collected for assays of antibody activity and specificity by conventional assays.

Large amounts of antibody are obtained from spent culture medium harvested from 150 mm plates or roller bottles. The medium is subsequently concentrated by means of a hollow-fiber concentrator (Amicon). Also, antibody is obtained from the ascites fluid of athymic (nude) mice (nu/nu) that were injected 2-3 weeks previously with about 1 billion cloned hybridoma cells. The ascites fluid is diluted with saline by flushing the peritoneal cavity of each mouse with saline, the diluted fluids from each mouse are pooled.

The monoclonal anti-CEA IgG is radiolabeled with I-131 by injection into a radionuclide vial containing $^{131}I$ (Amersham-Searle). The monoclonal anti-CEA IgG is injected at a concentration of 20 μg IgG per mCi $^{131}I$.

EXAMPLE 11

Preparation of a Melanin/Boron Antibody Conjugate

The monoclonal anti-CEA IgG of Example 10 is reacted with a three-fold molar excess of the melanin/boron complex of Example 9 in an aqueous solution at pH 8. The reaction proceeds overnight at about 0° C. The resultant conjugate is separated from unreacted melanin/boron complex by passage through a sizing column. The recovered conjugate is then stored as a sterile solution.

Any of the melanin/boron complexes of Example 9 may be used in the above reaction to form a melanin/boron antibody conjugate.

EXAMPLE 12

Neutron Capture Therapy of Tumors

A patient having a cervical cancer is injected with 0.9 mg of the melanin/boron antibody conjugate of Example 11. The injection is preferably in the form of three injections of 0.3 mg of conjugate spaced about 3-6 hours apart for a 1 gram tumor.

A collimated beam of thermal neutrons is focused on the tumor location, and the tumor is irradiated with an external neutron beam dose of 400-800 rads delivered over an 8-20 minute period. Optionally, the procedure may be repeated, but usually should not exceed a total dose of 3200 rads.

Any of the melanin/boron antibody conjugates of Example 11 may be used in the above described neutron capture therapy procedure.

EXAMPLE 13

Preparation of Cloned Human Tyrosinase

Cloned human tyrosinase is prepared using the method of Kwon, B.S. as described in the published PCT application WO 88/02372.

The tyrosinase is produced in E. coli strain MM 294. The λmel 34 cDNA (as described by Kwon, B.S. in the same PCT application) is fused to a Tac expression vector (U.S. Pharmacia Inc.) which has Trp and lac promotor together. The construct is expressed in the E. coli strain MM 294 and subsequently purified by affinity column chromatography.

This tyrosinase is then used to treat diseases caused by a melanin deficiency.

EXAMPLE 14

Introduction of Human Tyrosinase Gene Into a Defective HSV-1 Vector

A defective herpes simplex virus 1 (HSV-1) vector, pHSVlac, has been developed by Geller, A.I., et al., *Science* 241, 1667 (1988). This vector is useful for transporting genes through the blood brain barrier.

The vector, pHSVlac, contains the *Escherichia coli lacZ* gene which is under the control of the HSV-1 immediate early 4/5 promoter. Using conventional publicly available endonucleases, pHSVlac is digested at its EcoRI sites to remove the *E. coli lacZ* gene. The λ mel 34 human tyrosinase gene (described by Kwon, B.S. in PCT application WO 88/02372) is then inserted to pHSVlac in place of the *E. coli lacZ* gene, and the vector is religated using conventional techniques.

This chimeric pHSVlac vector may then be used to introduce the tyrosinase gene into patients suffering from diseases caused by a melanin deficiency.

EXAMPLE 15

Stably Transforming Cultured Peripheral Neurons with the pHSVlac Vector Expressing Tyrosinase Gene Primary cultures of dissociated neurons from dorsal root ganglia and superior cervical ganglia of newborn rats are prepared in accordance with the techniques taught by Hawrot, E. et al., *Methods Enzymol.* 58, 574 (1979). The cultures are then infected with the chimeric pHSVlac vector of Example 14, above, and incubated for 24 hours at 37° C. The cultures are then fixed and assayed for tyrosinase using antityrosinase antibodies (available from Dr. Seymour H. Pomerantz, Department of Biological Chemistry, University of Maryland School of Medicine, Baltimore, Md. 21201) and conventional techniques. Tyrosinase is found to be present in both the dorsal root ganglia cell cultures and the superior cervical ganglia cell cultures.

EXAMPLE 16

Transneuronal Transfer of the pHSVlac Vector Expressing Tyrosinase Gene

In accordance with the technique of Ugolini et al., *Science* 243, 89 (1989), eight rats (6 to 7 weeks old) are unilaterally injected in the ulnar and median nerves with the chimeric pHSVlac vector of Example 14, above. After four days, the rats are anesthetized and perfused with 10% Formalin as taught by Ugolini et al., *Brain Res.* 442, 242 (1987). The brains and spinal cords of the rats are cut into 60 μm transverse frozen sections, and the presence of tyrosinase is assayed using antityrosinase antibodies and conventional techniques as described in Example 15, above. Tyrosinase is found to be present in the rat brain neurons, due to the transneuronal transfer of the chimeric pHSVlac vector from its peripheral neuron injection site to the brain.

NEUROLOGICAL ANALYSIS EXAMPLES

The tests of Examples 17-19 below were conducted to analyze the neurological affects of the melanin analog produced by the method of Example 4. All of the tests described in the Examples below were completed within three minutes.

Thirty two male Long Evans rats were used in the neurological analyses. The rats were divided into 4 groups of 8 animals in each group. The first group received an injection of 1.0 mg/kg, the second group received an injection of 0.1 mg/kg, the third group received an injection of 0.01 mg/kg, and the last group received a 0.9% saline injection. All injections were administered I.P. 30 minutes prior to behavioral testing. All animals were injected once a day for four consecutive days. The animals were given the following tests in the described order:

EXAMPLE 17

Sensory Tests

A. Olfaction Orienting Test

Since normal rats will tend to orient to novel stimuli, two pungent (to humans) scents were used in this test (ammonia and Mennen Skin Bracer ®) to determine the effects of melanin analog on the olfactory orienting response. A cotton swab was moistened with either scent. Then the swab was brought from behind the animals's head toward the nose. The swab was not allowed to enter the animal's visual field nor was it allowed to touch the animal. The rating scale of response was 0 if no orienting response occurred and 1 if the animal oriented by sniffing at the swab. There were four tests (2 with each odor) brought from the right and the left sides. The average of the four tests was used as a index of olfactory detection.

B. Visual Stimulus Orienting Test

A 2×2 inch corrugated cardboard square was held by a pair of hemostats. This square was brought from behind the animal's head into its peripheral field of vision. The rating scale for response was the same as above. There were two tests, one from the right and the other from the left. The average of the two tests was used as an index of visual detection.

C. Somatosensory Orienting Tests

Using a Von Frey hair of 2 g pressure, the rat's shoulders, mid-section, and hindquarters were touched on both right and left sides. The average of six responses was used as an index for somatosensory detection.

D. Whisker Touch Orienting Test

A cotton swab was brought from behind the animal's head out of the animal's visual field and put in contact with the vibrissae successively on their right and left sides. The response recorded was based on the same scale as tests 1 and 2. The average of the two responses was used as an index of whisker touch detection.

E. Results

The effects of the various melanin doses on detection of olfactory cues, visual cues, somatosensory cues and whiskey touch were measured. In general, it was found that the melanin analog does not alter sensory function.

EXAMPLE 18

Sensory-Motor Tests

A. Placing Reflex Test

For this test the animal was suspended by the tail. While suspended the animal was brought close to the edge of a table. If the only stimulus necessary for forelimb extension was the sight of the table, it was rated as a 1, if it required the touch of the snout, the score was ½, if it required the maintenance of the snout touching the table, the score was ½, and if no response was elicited, a 0 was given.

B. Tilted Platform Test

Each animal was placed on the center of a 30×30 cm square of carpet-covered plywood. The plywood was tilted down to 30 degrees so that the rat's head was at the low end. If the animal responded normally it would turn around so its head faced up the slope. This response was given a 1. If the animal remained in the original position a 0 was given.

C. Results

The effects of the various melanin doses on performance of the placing reflex and the tilt reflex were measured. In general, the melanin analog does not alter sensory-motor function.

EXAMPLE 19

Motor Tests

A. Grasping Reflex

The rat was suspended by the nape of the neck then the palms of both front feet were touched by a single piece of stiff piano wire. Grasping is accomplished by flexion of the fingers around the wire. The rating scale used was 0 for no response, 1 for grasping the wire.

B. Righting Reflex (Rollover)

In this test the animal was held upside down 40 cm above a foam pad; then the animal was dropped. If the animal landed on the its feet a score of 1 was given, if anything else a 0.

C. Results

The effects of the various melanin doses on performance of the grasping reflex and two types of righting reflexes were measured. In general, it was seen that the melanin analog does not alter motor functions.

EXAMPLE 20

Food and Water Intake and Open Field Activity

One week after the completion of the neurological analysis, the animals were placed on a 23¾-hour water and 23½-hour food deprivation schedule. Water intake was measured once per day for the 15 minute water drinking period. Food intake was measured once per day for the 30 minute feeding period.

The animals were adjusted to this schedule for 5 days. On the sixth day, 30 minutes prior to the water and food intake period, the same groups of animals received the various melanin analog doses. On the seventh and eighth day, water and food intake were again measured.

The animals were then maintained on the food and water schedule for four more days. On the fifth day, the same groups of animals received the various melanin doses, and 30 minutes later they were tested in an open field. The open field for evaluating level of activity and emotionality consisted of a large wooden square box (120×120 cm) with 29 cm high walls. The floor of the box was painted white and divided by black lines into 64 square sections each measuring 15×15 cm. Thirty minutes after drug injection, each animal was placed in the center of the open field for a 10 minute period. The number of squares entered and the number of different activities (grooming, scratching, righting, washing, defecating and urinating) that were emitted during each minute was recorded. A "square entry" in the open field consisted of having all four feet within one square.

The effects of various dose levels on water intake on day 6 were examined. There appears to be a dose dependent decrease in water intake with marked reductions at the higher dose levels. There was total recovery of water intake the day after the melanin analog injection.

The effects of various dose levels on food intake on day 6 was also examined. There was a clear dose dependent reduction in food intake with marked reductions at the higher dose levels. Recovery of food intake to normal levels was seen the next day with the two lower drug levels. With the highest melanin dose, recovery of food intake was not seen until 2 days later. In general, the melanin analog affects normal food and water intake suggesting an influence on neural systems mediating variables that control level of motivation.

The effects of various melanin analog dose levels on general activity level (number of squares traversed in a 10 minute period) was also studied. Relative to saline or the low dose injection group, there is a marked reduction in overall level of locomotion in animals that received the higher dose levels (0.1 and 1.0 mg/kg). The effects of various melanin dose levels on activities other than locomotion (grooming, righting, scratching and washing) were measured. Relative to saline or the low dose injection group, there is a marked reduction in overall level of activity in animals that received the higher dose levels (0.1 and 1.0 mg/kg). The effects of various melanin analog dose levels on emotionality (defecation and urination) were studied as well. There appears to be some increase in the level of emotionality in the group that received the 0.1 mg/kg dose relative to the other groups. In general, the higher melanin analog doses produce a general inhibitory effect on locomotion and other behavioral activities, again suggesting a drug effect on motivation.

EXAMPLE 21

Acquisition of Radial Arm Maze

Due to the motivational effects of the high dose levels of the melanin analog, it was decided not to use the highest dose levels (1.0 mg/kg) for this experiment. Thus, 24 animals were food deprived and maintained at 80–85% of their ad lib. weight for at least one week. For the next 6 days all animals were adapted to the radial arm maze with food continuously available in the center and at the end of the arms.

Starting on the seventh day, 30 minutes prior to testing, the animals received either an 0.01 mg/kg (N=8), or 0.1 mg/kg (N=8), or a saline (N=8) injection. Each animal was placed in the center of the radial arm maze and allowed to visit the 8 arms which were baited with small pieces of Froot Loop ® cereal. Each animal was run until it had visited and consumed food at all 8 arms or until 15 minutes had elapsed. Reentry into an arm visited previously was scored as an error. The total number of errors to visit all 8 arms was used as the dependent measure. The above procedure was repeated once a day for 12 days.

The results indicate that all three groups learned the maze (showed a reduction in errors) at about the same rate, even though there is more day to day variability in the groups with the melanin analog injections. Also the melanin injected groups took more time to finish each trial. In general, the melanin analog does not appear to facilitate or impair acquisition of the radial arm maze. In conclusion, high levels of melanin analog do not impair sensory motor or motor functions, nor do they alter acquisition of a radial arm maze task, but this agent does alter motivational levels by inhibiting water and food intake and overall levels of activity and locomotion.

EXAMPLE 22

Melanin's Effect on Carotid Nerve Fibers

PROCEDURE

Melanins were tested for their effect on carotoid nerve fibers. The six substances were: F5H (melanin made in the presence of 5 mM Fe precipitated with Hcl at pH2), COH (melanin made in the presence of 1 mM Cu precipitated with HCl at pH2), F4E (melanin made in the presence of 4 mM Fe precipitated with two volumes of 95% ethanol), COE (melanin made in the presence of 1 mM Cu precipitated in the presence of two volumes of 95% ethanol), C47 (melanin precipitated with hCl at pH 2) and S23 (carborundum). The melanin analogs were tested against their solvent, and dopamine (DA). The solvent was 0.2 $NH_4OH$, at pH 7.4 adjusted with 1N HCl, referred to as $NH_4Cl$ or solvent.

The biological preparation used was the isolated rat carotid body with its nerve, superfused in vitro with oxygenated Tyrode's solution, pH 7.4 at 36° C. The superfusion flow was 1 ml/minute. The carotid body is an organ strategically located in the carotid bifurcation, that senses the changes $pO_2$, $pCO_2$ and pH of the arterial blood going to the brain. The sensory elements are the glomus cells. They are synaptically connected to the carotid nerve fibers which carry the information tot he central nervous system. These nerve fibers have dopaminergic receptors which are well identified biochemically and physiologically.

The carotid nerve discharges were recorded with platinum electrodes (0.2 mm diam.) and AC amplified. The nerve discharges were monitored in an oscilloscope and stored on tape for further analysis. Later, the nerve discharges were counted using a window discriminator and a digital counter. The impulse frequency was measured every second and registered on paper using a chart recorder. The data was analyzed using a Macintosh computer.

Some problems developed and were corrected during the experiments:

1) The melanin analogs precipitated when added to the perfusing solution. This problem was avoided by increasng the solvent volume.

2) DA oxydized when dissolved in the solvent. Thus, it was difficult to test DA again the melanin analogs using the same solvent. Therefore, DA had to be diluted in Tyrode's solution.

3) The solvent had has a stimulating effect on the chemosensory discharges of the carotid nerve due to the ammonium ions. Thus, to measure the potency of the melanin analogs the maximum discharge rate induced by the solvent was subtracted from the maximum discharge rate induced by the melanin analog. The resulting discharge frequency was termed $\Delta Fc$.

RESULTS

The basal spontaneous discharge of the biological preparation was stable along the experiments, and to avoid interaction between the substances being tested, the preparation was washed with superfusing solution for 10 to 15 minutes between melanin analog and control injections.

A. Effect of 100 μg Doses of Melanins

All of the samples tested were applied in 10 μl volumes and they produced discharge stimulation. For all the substances tested the stimulating effect was greater than that induced by the same volume of control solution (solvent). The injection of 10 μl of Tyrode's solution did not change the discharge frequency. COH and COE were the most potent substances, and the amplitude of their peak effects was not significantly different ($p<0.001$). Taking these effects as 100%, the response of the biological preparation to F5H was 27% lower, that of F4E was 54.2% lower and that of C47 and S23 was 59% lower.

B. Effect of 50 μl Doses of Melanins

In this part of the procedure, all of the samples were applied in 5 μl volumes. The effects of melanins decreased in amplitude as expected when lowering the dose. However, the application of 50 μg of F4E produced a discharge increase 61.7% greater than that induced by 100 μg of the same melanin analog. Also, the effect of C47 was about the same as that obtained with 100 μg of the same melanin analog. These results indicate that the dose response curves for these two melanin analogs should be shifted to the left.

C. Effects of DA and the Melanins

Dopamine produces two different effects on the biological preparation. Low doses (10–30 μg) produce discharge depression followed by stimulation. In contrast, large doses (50–300 μg) produce only discharge stimulation. Although DA could not be applied dissolved in $NH_4Cl$, its peak effects can still be compared to those induced by the melanin analogs.

Low doses of F5H had an effect very similar to that lo of DA. Therefore, it is possible that both F5H and DA may share the same receptor sites. This theory is supported by the finding that F5H is less potent when applied to the bath immediately after DA. Furthermore, when the application of F5H is spaced from DA, the response of the biological preparation to F5H is unaffected. This experiment should be repeated using dopamine receptor blockers to study this phenomenon in more detail. It is also interesting to note that in several experiments a sharp depression of the nerve discharges was observed during the rising phase of stimulation produced by some melanin analogs.

D. Duration of the Effect of Melanins

Another interesting finding is that the effect of the melanin analogs was 30% to 50% longer than that of DA. Also, the effect of the melanins lasted longer than the effect of the solvent. This could indicate a stronger binding of melanins to the receptor sites or a slower inactivation mechanism for these substances.

CONCLUSIONS

There is extensive evidence that the carotid nerve endings have dopamine receptors. The above results show that the carotid body and/or nerve also has receptor sites for melanin analogs. This conclusion is supported by the dose dependent effects reported in the results.

The effects of melanins on the biological preparation are more potent than DA and last 2-3 times longer. The most potent effects for larger doses (100 μg) of melanins were those induced by COE and COH. However, for lower doses (50 μg) F4E induced a very potent discharge stimulation. The smaller effect of F5E at higher doses could be explained by receptor desensitization, a well known phenomenon in synaptic physiology. In decreasing order of potency would follow COE COH F5H C47 and 523.

In view of these results, F4E is the most potent substance. An analysis of response curves shows that F4E and CDE are the most potent with F4E having the strongest effect. This differences in potency is clearly seen at doses of 10 μg at which there is statistically significant difference between F4E and CDE ($p<0.001$). At a dose of 25 μg, there is not a statistically significant difference between F4E and CDE.

It is also important to consider that all of the substances were applied to the bath as a bolus, diluted in saline and at a distance of 1 mm from the preparation. Since there was a continuous flow of saline in the recording bath, the actual concentration of the substance of the carotid body would be less, perhaps as much as a 50% dilution.

Although it is unclear if melanins and DA share the same receptor sites, the depression of the effect of F5H by previous application of DA is an indicator that this may be true.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for treating a mammal having Parkinson's disease, comprising administering to the mammal an effective amount of an active substance which causes an increase in the concentration of melanin in the tissue, said active substance being selected from the group consisting of melanin, melanin derivatives, melanin analogs, melanin variants, and combination thereof, and wherein said active substance is administered in a manner to effectively reduce the effects of Parkinson's disease.

2. The method of claim 1 wherein prior to administration of said active substance, the mammal is treated to relax the blood-brain barrier.

3. The method of claim 1 wherein the active substance is melanin.

4. A method for treating a mammal having Parkinson's disease, comprising administering to the mammal an effective amount of an active substance which causes an increase in the concentration of melanin in the tissue, said active substance being selected from the group consisting of melanin, melanin derivatives, melanin analogs, melanin variants, and combination thereof, wherein prior to administration of said active substance, the mammal is treated to relax the blood-brain barrier, wherein said treatment for relaxing the blood-brain barrier is the sugar loading of the blood system.

5. A method for treating a mammal having Parkinson's disease, comprising administering to the mammal an effective amount of an active substance which causes an increase int he concentration of melanin in the tissue, said active substance being selected from the group consisting of melanin, melanin derivatives, melanin analogs, melanin variants, and combination thereof, wherein prior to administration of said active substance, the mammal is treated to relax the blood-brain barrier wherein said treatment for relaxing the blood-brain barrier is the administration of melanin or melanin derivatives.

* * * * *